United States Patent [19]

Ryan et al.

[11] Patent Number: 4,690,936
[45] Date of Patent: * Sep. 1, 1987

[54] ANTI-HYPERTENSIVE AGENTS

[75] Inventors: James W. Ryan; Alfred Chung, both of Miami, Fla.

[73] Assignee: University of Miami, Coral Gables, Fla.

[*] Notice: The portion of the term of this patent subsequent to Sep. 1, 2004 has been disclaimed.

[21] Appl. No.: 145,772

[22] Filed: May 2, 1980

Related U.S. Application Data

[63] Continuation-in-part of Ser. No. 127,472, Mar. 5, 1980.

[51] Int. Cl.$^4$ .................... A61K 31/40; A61K 31/41; C07D 207/00; C07D 211/72
[52] U.S. Cl. ..................... 514/362; 514/363; 514/308; 514/423; 514/255; 548/531; 548/535; 546/310
[58] Field of Search ................. 260/112.5 R; 548/531, 548/535; 546/310; 514/362, 363, 308, 423, 255

[56] References Cited

U.S. PATENT DOCUMENTS

| | | | |
|---|---|---|---|
| 3,832,337 | 8/1974 | Ondetti | 260/112.5 |
| 3,891,616 | 6/1975 | Ondetti | 260/112.5 |
| 3,947,575 | 3/1976 | Ondetti | 424/177 |
| 4,046,889 | 9/1977 | Ondetti | 424/319 X |
| 4,052,511 | 10/1977 | Cushman | 424/274 |
| 4,053,651 | 10/1977 | Ondetti | 424/319 X |
| 4,070,361 | 1/1978 | Petrillo | 260/293.85 |
| 4,091,024 | 5/1978 | Ondetti | 260/293.63 |
| 4,105,776 | 8/1978 | Ondetti | 424/274 |
| 4,105,789 | 8/1978 | Ondetti | 424/309 |
| 4,108,886 | 8/1978 | Ondetti | 260/455 R |
| 4,113,715 | 9/1978 | Ondetti | 424/274 |
| 4,116,962 | 9/1978 | Ondetti | 260/293.63 |
| 4,129,566 | 12/1978 | Ondetti | 546/326 |
| 4,146,611 | 3/1979 | Ondetti | 424/177 |
| 4,151,172 | 4/1979 | Ondetti | 260/326.2 |
| 4,154,840 | 5/1979 | Ondetti | 424/267 |
| 4,154,934 | 5/1979 | Bernstein | 546/189 |
| 4,154,935 | 5/1979 | Ondetti | 546/189 |
| 4,154,937 | 5/1979 | Cushman | 546/221 |
| 4,168,267 | 9/1979 | Petrillo | 260/326.2 |

FOREIGN PATENT DOCUMENTS 0009898 4/1980 European Pat. Off. ...... 260/112.5 R

OTHER PUBLICATIONS

Cushman et al. Biochemistry, vol. 16, 1977, p. 5484.
Cushman et al. Experientia, vol. 29, 1973, p. 1032.
Ondetti et al. Science, vol. 196, 1977, p. 441.
Dorer et al. Biochem. Biophys. Acta, vol. 429, 1976, p. 220.
Fisher et al. Arch. Biochem. Biophys., vol. 189, 1978, p. 81.
Gavras et al., N.E. J. Med, vol. 291, 1974, p. 817.
Gavras et al., NE J Med, vol. 298, 1978, p. 991.
Lipmann, Accounts Chem Res., vol. 6, 1973, p. 6.
Lehninger, Biochemistry, Worth Pub. NY, 1970, pp. 153-157.
Ryan et al., Tissue & Cell, vol. 10, 1978, p. 555.
Fischer et al. Ber., vol. 33, 1900, pp. 2383-2393.
Fischer et al., Febs Letters, vol. 107, 1979, pp. 273-275.

Primary Examiner—Delbert R. Phillips

[57] ABSTRACT

Novel inhibitors of angiotensin converting enzyme having the general formula R—A—S—Z are disclosed as potent inhibitors of angiotensin converting enzyme and are useful anti-hypertensive agents.

54 Claims, No Drawings

ANTI-HYPERTENSIVE AGENTS

CROSS-REFERENCE TO RELATED APPLICATION

This is a continuation-in-part of Ser. No. 127,472, filed Mar. 5, 1980, which is incorporated herein by reference as though set forth in full.

BACKGROUND OF THE INVENTION

Angiotensin converting enzyme (peptidyldipeptide hydrolase, hereinafter referred to as ACE) occupies a central role in the physiology of hypertension. The enzyme is capable of converting the decapeptide angiotensin I, having the sequence

AspArgValTyrIleHisProPheHisLeu to an octapeptide, angiotensin II, by removal of the carboxy-terminal HisLeu. The symbols for various chemical entities are explained in the following table:
- Ala=L-alanine
- Arg=L-arginine
- Asp=L-aspartic acid
- <Glu=pyro-L-glutamic acid
- Gly=glycine
- Hip=Hippuric acid (Benzoyl-glycine)
- His=L-histidine
- Ile=L-isoleucine
- Leu=L-leucine
- Phe=L-phenylalanine
- Pro=L-proline
- ΔPro=L-3,4-dehydroproline
- Ser=L-serine
- Trp=L-tryptophan
- Tyr=L-tyrosine
- Val=L-valine
- ACE=Angiotensin converting enzyme
- Hepes=N-2-hydroxyethylpiperazine-N'-2-ethanesulfonic acid Angiotensin I is formed by the action of the enzyme renin, an endopeptidase found in kidney, other tissues and plasma, on a serum α-2 globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors. [Gavras, I., et al., *New Engl. J. Med.* 291, 817 (1974)].

Ace is a peptidyldipeptide hydrolase. It catalyzes the hydrolysis of the penultimate peptide bond at the C-terminal end of a variety of acylated tripeptides and larger polypeptides having an unblocked α-carboxyl group. The action of ACE results in hydrolytic cleavage of the penultimate peptide bond from the carboxyl-terminal end yielding as reaction products a dipeptide and a remnant.

The reactivity of the enzyme varies markedly depending on the substrate. At least one type of peptide bond, having the nitrogen supplied by proline, is not hydrolyzed at all. The apparent Michaelis constant ($K_m$) varies from substrate to substrate over several orders of magnitude. For general discussion of the kinetic parameters of enzyme catalyzed reactions, see Lehninger, A., *Biochemistry*, 2nd Ed., Worth Publishers, Inc., New York, 1975, pp. 189–195. Many peptides which are called inhibitors of the enzymatic conversion of angiotensin I to angiotensin II are in fact substrates having a lower $K_m$ than angiotensin I. Such peptides are more properly termed competitive substrates. Examples of competitive substrates include bradykinin, and the peptide $BPP_{5a}$ (also called SQ20475) from snake venom, whose sequence is <GluLysTrpAlaPro.

Numerous synthetic peptide derivatives have been shown to be ACE inhibitors by Ondetti, et al. in U.S. Pat. No. 3,832,337 issued Aug. 27, 1974.

The role of ACE in the pathogenesis of hypertension has prompted a search for inhibitors of the enzyme that could act as antihypertensive drugs. See for example U.S. Pat. Nos. 3,891,616, 3,947,575, 4,052,511 and 4,053,651. A highly effective inhibitor, with high biological activity when orally administered, is D-3-mercapto-2-methylpropanoyl-L-proline, designated SQ14225, disclosed in U.S. Pat. No. 4,046,889 to Ondetti et al., issued Sept. 6, 1977, and in scientific articles by Cushman, D. W. et al., *Biochemistry* 16, 5484 (1977), and by Ondetti, M. et al., *Science* 196, 441 (1977). The inhibitor SQ14225 reportedly has an $I_{50}$ value of $2.3 \times 10^{-8}M$. The $I_{50}$ value reported by Cushman, et al., supra is the concentration of inhibitor required to produce 50% inhibition of the enzyme under a standard assay system containing substrate at a level substantially above $K_m$. It will be understood that $I_{50}$ values are directly comparable when all potential factors affecting the reaction are kept constant. These factors include the source of enzyme, its purity, the substrate used and its concentration, and the composition of the assay buffer. All $I_{50}$ data reported herein have been performed with the same assay system and same enzyme (human urinary ACE) and with an approximately ½ $K_m$ level of substrate and are therefore internally consistent. Discrepancies with data obtained by other workers may be observed. Indeed such discrepancies do exist in the literature, for unknown reasons. See, for example, the $I_{50}$ values for $BPP_{9a}$ reported by Cushman, D. W., et al., *Experientia* 29, 1032 (1973) and by Dorer, F. E., et al., *Biochim. Biophys. Acta* 429, 220 (1976).

The mode of action of SQ14225 has been based upon a model of the active site of ACE developed by analogy with the better known related enzyme, carboxypeptidase A. The active site was postulated to have a cationic site for binding the carboxyl end group of the substrate and a pocket or cleft capable of binding the side chain of the C-terminal amino acid and providing especially tight binding for the heterocyclic ring of a terminal proline residue. A similar pocket for the penultimate amino acid residue was postulated, and the published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as a methyl group, and an S-acetyl derivative, substantially reduced potency of the inhibitor. See Cushman, D. W., et al., *Biochemistry*, supra.

In vitro study of the mechanism by which SQ14225 and its analogs act to inhibit ACE has been somewhat hampered by the instability of these molecules under ambient conditions. For example, it has been observed that a fresh aqueous solution of concentration, e.g., 1 mg per ml of SQ14225 at a pH of about 8 becomes substantially less active upon standing for as little as 30 minutes, and that activity continues to decrease as the solution stands for longer periods. It is believed that this loss in activity is mainly the result of dimerization of SQ14225 occurring at the sulfhydryl end groups, whereby a disulfide is formed which is largely inactive as an inhibitor. Since the free sulfhydryl group is highly reactive and may be readily oxidized to polar acidic moieties such as sulfone and sulfoxide groups, it may also be that the observed in vitro loss of activity of aqueous solutions of SQ14225 on standing is in some part a consequence of one or more such oxidation reactions, with formation of a sulfone or sulfoxide which does not function effectively as an inhibitor for ACE.

Such reports of SQ14225 clinical testing as are currently available, some of which refer to the compound under the name "Captopril", suggest that the product is sufficiently stable in the normal gastric and intestinal environments of most patients to be an effective inhibitor for ACE when administered orally. It is not yet clear, however, whether there may be a group of patients for which SQ14225 is substantially ineffective. Because of the high reactivity of the free sulfhydryl group, SQ14225 could readily form mixed disulfides with serum, cellular proteins, peptides or other free sulfhydryl group-containing substances in the gastric or intestinal environments, in addition to the possibility for dimer formation or oxidative degradation reactions. A mixed disulfide with protein may be antigenic and, indeed, occasional allergic reactions have been clinically observed. See Gavras, et al., *New England J. Med.* 298, 991 (1978). Disulfides and oxidative degradation products of SQ14225, if formed, may at best be expected to be largely ineffective as inhibitors. It may be postulated accordingly that dose response to SQ14225 may vary with conditions of administration and among individual patients. Moreover, in at least some patients, unwanted side effects may occur and maintenance of an effective concentration of the inhibitor in the body may be difficult to control.

Thioester compounds generally are thought to be highly reactive in that the thioester linkage is readily hydrolyzable to a sulfhydryl moiety and a carboxylic moiety. Thioesters are accordingly often used as active ester intermediates for acylation under mild conditions. Such groups as, e.g., acetylthio have been used as blocking groups in the above cited Ondetti, et al. patents. Thioester intermediates are also postulated to occur in the biosynthesis of cyclic peptides such as tyrocidin or gramicidin S. See Lipmann, F. in *Accounts Chem. Res.* 6, 361 (1973).

Thioester compounds having potent ACE inhibitory activity and oral effectiveness as anti-hypertensive agents have been disclosed in copending applications (Ser. Nos. 064,897 through 064,903, all filed on Aug. 14, 1979, Ser. Nos. 161,150 and 161,151, both filed on Jan. 30, 1980 and Ser. No. 121,188, filed on Mar. 3, 1980. All copending applications are incorporated herein by reference.

Compounds related to SQ14225 have been disclosed by Ondetti, et al., U.S. Pat. Nos. 4,046,889, 4,052,511, 4,053,651, 4,113,715 and 4,154,840. Of interest are disclosed analogs of SQ14225 having the five-membered heterocyclic ring of proline replaced by a four- or a six-membered ring. The inhibitory potencies of such analogs relative to SQ14225 are not disclosed. Substitution of D-proline for L-proline is reported to drastically reduce inhibitory potency of 3-mercaptopropanoyl amino acids (Cushman, D. W., et al., supra).

The substitution of L-3,4-dehydroproline for proline has been studied in several systems. Substitution of L-3,4-ΔPro in the 7 position of bradykinin yields a bradykinin derivative which has significantly reduced physiological activity. See Fisher, G. H. et al., *Arch. Biochem. Biophys.* 189, 81 (1978). On the other hand, substitution of L-3,4-ΔPro at the 3, 5, 8 or 9 position in ACE inhibitor BPP$_{9a}$ enhances its inhibitory activity. See Fisher, G. H. et al., *FEBS Letters* 107, 273 (1979). In copending application Ser. No. 161,151, applicants found that the compounds having ΔPro, which are disclosed in said application, have high inhibitory potency and antihypertensive effectiveness. However, at present, no rationale can be advanced to explain the diversity of observed results following substitution of ΔPro for proline. Similarly, no clear picture has emerged of the effects of other proline derivatives or analogs substituted at various loci on ACE inhibitors.

To date, the effect of the amino acid to the left of the sulfur in the thioester compounds disclosed in our copending applications, has not been determined. It is thought that this amino acid functions as an additional recognition site for the enzyme. If this is true, it would be expected that a compound with an amino acid here would be a better inhibitor. Applicants have found that various amino acids are effective and that the hydroxyprolines, proline, L-, and D,L-3,4-dehydroproline, thiazolidine-4-carboxylic acid and L-5-oxo-proline derivatives are all effective anti-hypertensive agents and have high inhibitory potency for ACE.

SUMMARY OF THE INVENTION

Novel inhibitors of ACE are disclosed which have the general formula

$$R-A-S-Z \qquad (I)$$

wherein,

R is hydrogen, formyl, acetyl, propanoyl, butanoyl, phenylacetyl, phenylpropanoyl, benzoyl, cyclopentanecarbonyl, tert-butyloxycarbonyl, cyclopentanecarbonyl-L-lysyl, pyro-L-glutamyl-L-lysyl, L-arginyl, L-lysyl or pyro-L-glutamyl;

A is phenylglycine, β-benzyl aspartic acid, γ-benzyl glutamic acid, S-benzyl cysteine, O-benzyl serine, O-benzyl tyrosine, O-benzyl threonine, β-phenyl serine, thyronine, β-2-thienylserine, β-2-thienylalanine, α-methyl histidine, α-methyl tyrosine, α-methyl phenylalanine, α-methyl tryptophan, substituted tyrosine wherein the substituent is halo, nitro, methoxy or hydroxy, substituted phenylalanine wherein the substituent is halo, nitro, amino or methoxy or substituted trytophan wherein the substituent is fluoro, methyl or methoxy, the α-amino group thereof being in amide linkage respectively with R, and the carboxyl group thereof being in thioester linkage with S;

S is a sulfur atom in thioester linkage with A and Z;

Z is

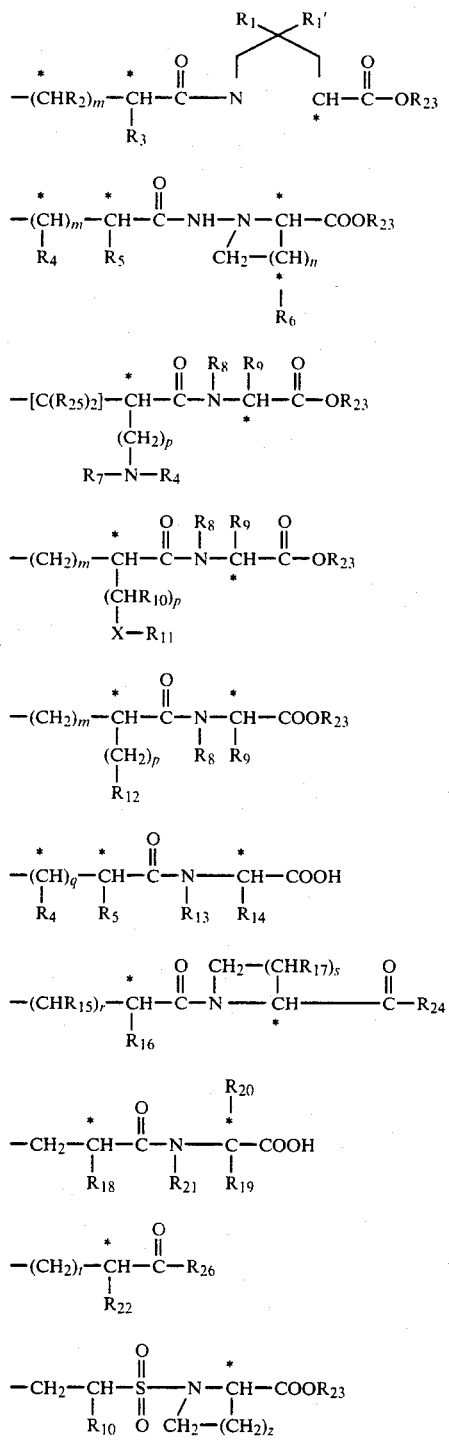

$R_1$ is hydrogen or halogen;
$R_1'$ is hydrogen or halogen;
$R_2$ is hydrogen, lower alkyl or trifluoromethyl;
$R_3$ is hydrogen, lower alkyl or trifluoromethyl, not more than one of $R_2$ and $R_3$ being trifluoromethyl, and at least one of $R_1$, $R_1'$, $R_2$ or $R_3$ is a halogen or trifluoromethyl substituent represented by the named symbol above;

$R_4$ is hydrogen, lower alkyl or phenyl-lower alkylene;

$R_5$ is hydrogen, lower alkyl or phenyl-lower alkylene;

$R_6$ is hydrogen or hydroxy or when n=2, $R_6$ can also be halogen;

$R_7$ is hydrogen, lower alkanoyl or amino(imino)methyl;

$R_8$ is hydrogen, lower alkyl or hydroxy-lower alkylene;

$R_9$ is hydrogen, lower alkyl, phenyl, phenyl-lower alkylene, hydroxy-lower alkylene, hydroxyphenyl-lower alkylene, amino-lower alkylene, guanidino-lower alkylene, mercapto-lower alkylene, lower alkyl-thio-lower alkylene, imidazolyl-lower alkylene, indolyl-lower alkylene, carbamoyl-lower alkylene or carboxy-lower alkylene;

or $R_8$ and $R_9$ together form a $(CH_2)_v$ bridge which completes a ring of 5 or 6 atoms with the nitrogen and carbon to which they are attached, one carbon optionally bearing a hydroxy group when v=4, one carbon optionally bearing a hydroxy group or halogen group when v=3;

$R_{10}$ is hydrogen or lower alkyl;

$R_{11}$ is hydrogen, lower alkyl or lower alkanoyl;

$R_{12}$ is carboxy, lower alkoxycarbonyl, carbamoyl, N-substituted carbamoyl or cyano;

$R_{13}$ is hydrogen, lower alkyl or phenyl-lower alkylene;

$R_{14}$ is hydrogen, lower alkyl, phenyl-lower alkylene, hydroxy-lower alkylene, amino-lower alkylene, guanidino-lower alkylene, imidazolyl-lower alkylene, indolyl-lower alkylene, mercapto-lower alkylene, lower alkyl-thio-lower alkylene, carbamoyl-lower alkylene or carboxy-lower alkylene;

$R_{15}$ is hydrogen, lower alkyl, phenyl or phenyl-lower alkylene;

$R_{16}$ is hydrogen, lower alkyl, phenyl or phenyl-lower alkylene;

$R_{17}$ is hydrogen, hydroxy or lower alkyl or when s=2, $R_{17}$ can also be halogen;

$R_{18}$ is hydrogen or lower alkyl;

$R_{19}$ is lower alkyl;

$R_{20}$ is lower alkyl;

$R_{21}$ is hydrogen or lower alkyl;

or $R_{19}$ and $R_{20}$ form a $(CH_2)_w$ bridge which completes a ring of 5 atoms with the carbon to which they are attached;

or $R_{19}$ and $R_{21}$ together form a $(CH_2)_x$ bridge which completes a ring of 5 atoms with the nitrogen and carbon to which they are attached;

$R_{22}$ is hydrogen or lower alkyl;

$R_{23}$ is hydrogen or lower alkyl;

$R_{24}$ is hydroxy, amino or lower alkoxy;

$R_{25}$ is hydrogen or when m=1, p=0, $R_4$=H and $R_7$=lower alkanoyl, then $R_{25}$ is hydrogen or lower alkyl;

$R_{26}$ is 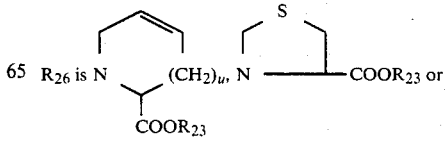

-continued

X is O or S;
m, t and u each is 0 or 1;
n and s each is 1, 2 or 3;
p is 0, 1, 2, 3 or 4;
q and r each is 0, 1 or 2;
v is 3 or 4;
w is 4;
x is 3; and
z is 2 or 3;

The asterisks indicate asymmetric carbons. The disclosed compounds are inhibitors of ACE and are useful as antihypertensive agents.

DETAILED DESCRIPTION OF THE INVENTION

The invention in its broad aspects includes thioester compounds which contain at least one amino acid or closely related structure, i.e. amino acid analog, and preferably two amino acids. These amino acids may be substituted or unsubstituted. The thioester compounds disclosed herein all contain one amino acid or closely related structure represented by A in formula I. It is preferred that the thioester compounds of this invention contain an acyl derivative of A represented by R-A in formula I. It is also preferred that a second amino acid be present in these thioester compounds. If a second amino acid is present, it is found in the group represented by Z in formula I.

The A portion of the thioester compounds may be selected from the group comprising those compounds listed in formula I. Examples of substituted amino acids include among others: 4-nitro-phenylalanine, 5-fluoro-tryptophan and O-benzyl threonine. The preferred acyl derivative R, described above, is in amide linkage with the α-amino group of A. Of these acyl derivatives, benzoyl is preferred. While it is preferred the A be in the L-form, it may also be in the D-form or racemic in form.

When A is a substituted tyrosine or phenylalanine, the halogen may be selected from the group consisting of F, Cl, Br or I. When phenylalanine is substituted by halo, nitro, amino or methoxy, it is preferably at position 4 of the phenyl ring. It is preferred that tyrosine be substituted at position 3 of the phenyl ring when the substituent is halo, nitro, hydroxy or methoxy. Tyrosine may also be di-substituted, preferably at positions 3 and 5 of the phenyl ring, when the substituent is halo. When tryptophan is substituted with fluorine, it is preferably at either position 5 or 6 of the indole ring. When the substituent is methyl, it may be at either position 4, 5, 6 or 7 of the indole ring. It is preferable that the methoxy substituent on tryptophan be at position 5 of the indole ring.

The remaining portion of the thioester compounds of this invention is represented by Z in formula I. Z is selected from the group of compounds having formulas II-XI. It is preferred that Z contain an amino acid. Although any amino acid may be utilized, it is preferred that proline, hydroxyproline, 3,4-dehydroproline, 5-oxo-proline or a closely related structure such as thiazolidine-4-carboxylic acid be utilized. It is preferred that the amino acid in Z be in the L-form.

The lower alkyl groups represented by any of the variables include straight and branched chain hydrocarbon radicals containing one to seven carbon atoms. The lower alkylene groups are of the same kind also having one to seven carbon atoms. Similarly, the lower alkoxy groups are of the same kind having one to seven carbon atoms with a link to oxygen. The lower alkanoyl groups are the acyl radicals of the lower fatty acids having one to seven carbon atoms. The amino(imino)methyl group represented by $R_7$ is the residue of the guanidino radical

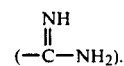

The N-substituted carbamoyl of $R_{12}$ is carbamoyl substituted at the nitrogen position with a lower alkyl or phenyl-lower alkylene. The halogen may be selected from the group consisting of F, Cl, Br or I.

The compounds of formula I can be produced by various methods of synthesis. According to a preferred method, R—A and HS—Z are coupled to produce R—A—S—Z. For this coupling, any conventional coupling agent in preferably an anhydrous medium may be used. In another preferred method, R—A—SH is coupled with halo-Z to produce R—A—S—Z using conventional coupling methods. In a third preferred method, R—A—SH is coupled with a vinyl-Z to produce R—A—S—Z by heating. For a particular desired thioester compound, one method may be more preferred than the others. Examples of suitable coupling agents are 1,1'-carbonyldiimidazole, dicyclohexylcarbodiimide, ethoxyacetylene or diphenylphosphoryl azide. Examples of suitable anhydrous medium are tetrahydrofuran (THF), dichloromethane, dioxane or dimethylformamide (DMF) although any other suitable anhydrous medium may be used.

The group R—A where R is benzoyl may be obtained commercially or is synthesized using the procedure described in copending application Ser. No. 116,950 incorporated herein by reference. The group R—A where R is formyl, acetyl, propanoyl, butanoyl, phenylacetyl, phenylpropanoyl or tert-butyloxycarbonyl (Boc) may be obtained commercially or is synthesized using the procedure described in copending application, Ser. No. 116,950.

Reactants which are commercially available refer to those reactants which can be obtained from standard chemical and biochemical supply companies. Examples of such companies include Alrdrich Chemical Company, Inc., Metucken, N.J. and Sigma Chemical Co., St. Louis, Mo.

The group R—A where R is cyclopentanecarbonyl is synthesized using the procedure described in copending application Ser. No. 064,901 incorporated herein by reference. The group R—A where R is cyclopentanecarbonyl-L-lysyl or pyro-L-glutamyl-L-lysyl is synthesized using the procedure described in copending application Ser. No. 064,902 incorporated herein by reference. The group R—A where R is L-arginyl, L-lysyl or pyro-L-glutamyl is synthesized using the procedure described in copending application Ser. No. 064,903 incorporated herein by reference.

The HS—Z group can be produced by various methods of synthesis. For this description, the synthesis of HS—Z where Z is formula VIII will be utilized for illustration purposes only. The process of forming HS—Z where Z is any of the formulas II–XI is done in a similar manner.

According to the preferred method, the imino group of formula VIII, i.e.

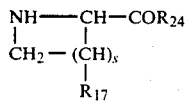 (XII)

wherein $R_{17}$, $R_{24}$ and s are defined above, is acylated with an acid of the formula

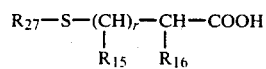 (XIII)

wherein $R_{15}$, $R_{16}$ and r are defined above and $R_{27}$ is hydrogen, lower alkyl, phenyl, substituted phenyl wherein the phenyl substituent is halogen, lower alkyl or lower alkoxy, phenyl-lower alkylene, diphenyl-lower alkylene, triphenyl-lower alkylene, lower alkyl-thiomethyl, phenyl-lower alkylthiomethyl, lower alkanoylamidomethyl or

wherein $R_{28}$ is hydrogen, hydroxy or lower alkyl. Preferably $R_{27}$ is acetyl. The acylation can be effected in the presence of a coupling agent in anhydrous medium. Any coupling agent and anhydrous medium may be utilized as previously described. Or the acid of formula XIII can first be activated prior to reaction with the amino group of formula XII involving formation of a mixed anhydride, symmetrical anhydride, acid chloride, active ester, Woodward reagent K or the like. For a review of the methods for acylation see *Methoden der Organischen Chemie* (Houben-Weyl), Vol. XV, part II, page 1 et seq. (1974). Deprotection, i.e. removal of $R_{27}$ when $R_{27}$ is not H, of the product of the acylation of XII with XIII can be effected by conventional means such as treatment with hot trifluoroacetic acid, cold trifluoromethanesulfonic acid, mercuric acetate, sodium in liquid ammonia or the like. For a review of these methods see *Methoden der Organische Chemie* (Houben-Weyl), Vol. XV, part I, page 376 et seq. (1974). When $R_{27}$ is the preferred

the product is preferably deprotected by ammonolysis.

Another method of forming HS—Z as illustrated by Z of formula VIII is to react the amino group of formula XII with ω-haloalkanoic acids of the formula

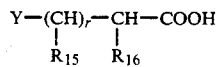 (XIV)

wherein Y is bromo, chloro or iodo to form

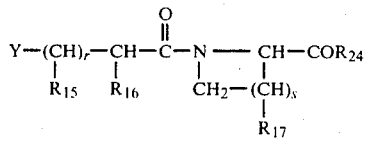 (XV)

This product is then subjected to displacement or addition with the anion of a thiol or a thioacid of the formula $R_{27}$—SH. The acid of formula XIV is first activated as previously described. The reaction of XIV and XII is conducted in an alkaline medium, for example alkali metal hydroxide, alkali metal bicarbonate, or alkali metal carbonate. The reaction of XV with $R_{27}$—SH is also conducted in an alkaline medium, preferably alkali metal carbonate. Deprotection is accomplished as described above.

Another method of forming HS—Z as illustrated by Z of formula VIII is to react the amino group of formula XII with thiolactones of the formula

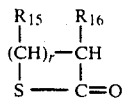 (XVI)

to yield the desired product HS—Z. This reaction is conducted in an anhydrous medium such as THF or the like.

A variation of this procedure involves the use of an acrylic acid of the formula

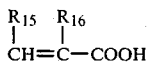 (XVII)

as starting material. This acrylic acid is first converted to the acid halide and reacted with the amino group XII to obtain the following product

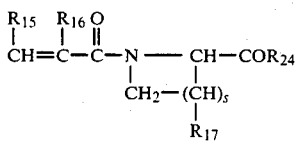 (XVIII)

This product is then subjected to the addition of a thiol or a thioacid of the formula $R_{27}$—SH as described above. The reaction of the acrylic acid with the amino group of formula XII is conducted in an alkaline medium, preferably an alkali metal carbonate.

Alternatively, the acrylic acid of formula XVII can be reacted with a thioacid of the formula $R_{27}$—SH to form

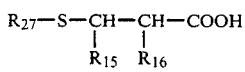 (XIX)

which is converted to the acid halide and reacted with the amino group of formula XII.

When an acid of the imino group of formula XII, i.e. when $R_{24}$ is hydroxy, is used as starting material, the final product obtained as the free carboxylic acid can then be converted to its ester, for example by esterification with a diazoalkane, like diazomethane, 1-alkyl-3-p-tolyltriazene, like 1-n-butyl-3-p-tolyltriazene or the like.

Treatment of the ester, preferably the methyl ester, with an alcoholic ammonia solution, converts the free acid to the amide, i.e. $R_{24}$ is $NH_2$. When an ester of the amino group of formula XII is used as starting material, the final product obtained can be treated with trifluoroacetic acid and anisole to remove the ester group ($R_{24}$) to yield the free carboxylic acid.

The thioester compounds of the formula A—S—Z, i.e. R is hydrogen, is prepared preferably by deprotecting the thioester compounds $N^\alpha$-tert-butyloxycarbonyl-A—S—Z. One method of deprotecting these compounds is described in copending application Serial No. 064,899 incorporated herein by reference.

Where Z is defined by formula XI, the HS—Z compounds are preferably synthesized by reacting the amino group with a haloalkylsulfonyl halide in an organic base such as N,N-dimethylaniline, N-methylmorpholine or the like in an inert organic solvent such as THF, dioxane, dichloromethane or the like. The product from this reaction is reacted with $R_{27}$—SH in the presence of an organic base and organic solvent as described above to yield HS—Z(XI).

pling agents to produce $N^\alpha$-Boc-thionorleucine phenyl ester. It is preferred that this be done by using the mixed anhydride coupling method in ethanol. The product is then reacted with NaSH in ethanol and under nitrogen to produce $N^\alpha$-Boc-thionorleucine. An alternative method for producing $N^\alpha$-Boc-thionorleucine is to react $N^\alpha$-Boc-norleucine with $H_2S$ using a mixed anhydride coupling method as described in Cronyn, M.W., et al., *J. Am. Chem. Soc.* 74, 4726 (1952). The $N^\alpha$-Boc-thionorleucine is then reacted with a compound of Formula XVIII, for example, by heating in toluene to produce $N^\alpha$-Boc-norleucine-S—Z. Alternatively, the $N^\alpha$-Boc-thionorleucine can be reacted with the compound of Formula XV to produce $N^\alpha$-Boc-norleucine-S—Z. For a more detailed description of the above-described method see copending application Ser. No. 128,953, filed on Mar. 10, 1980, incorporated herein by reference.

The thioester compounds of formula I have one or more asymmetric carbons. The following compound using R=benzoyl, A=Phe and Z of formula VIII is used for illustration purposes only. In the compound,

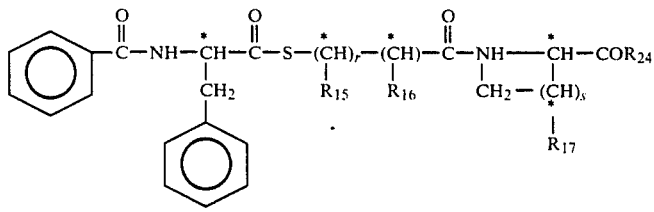

The amino group of Z defined by formula III is derived from nitrosoazetidine-2-carboxylic acid, nitrosoprolines or nitrosopipecolic acids which have the formula

(XX)

and which are prepared from the corresponding azetidine-2-carboxylic acid, proline or pipecolic acid, respectively, by means of nitroxyl tetrafluoroborate according to the method of Lijinsky et al., *Tetrahedron* 26, 5137 (1970). They can also be produced by the method described by Nagasawa et al., *J. Med. Chem.* 16, 583 (1973).

The nitroso amino acid of formula III is next reduced to the N-amino derivative which has the formula

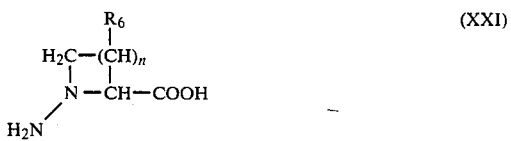

(XXI)

e.g., with zinc-acetic acid by the method described by Klosterman et al., *Biochemistry* 6, 173 (1967).

The R—A—SH group can be synthesized by various methods. For purposes of illustration only, the synthesis of R—A—SH where R is $N^\alpha$-tert-butyloxycarbonyl (Boc) and A is norleucine is shown.

According to the preferred method, thiophenol is coupled to $N^\alpha$-Boc-norleucine using conventional couthe possible asymmetric carbons are indicated by an asterisk. When $R_{15}$, $R_{16}$ or $R_{17}$ is other than hydrogen the carbon to which it is attached is asymmetric. The other carbons marked by an asterisk above are asymmetric. The compounds accordingly exist in sterioisomeric forms or in racemic mixtures thereof. All of these are within the scope of the invention. The above described synthesis can utilize the racemate or one of the enantiomers as starting material. When the racemic starting material is used in the synthetic procedure or a racemic mixture results from the synthesis, the stereoisomers obtained in the product can be separated by conventional chromatographic or fractional crystallization methods. In general, the L-isomer with respect to the carbon of the amino group constitutes the preferred isomeric form. Also the d-isomer with respect to the α-carbon in the acyl side chain (e.g. the carbon bearing $R_{16}$ in the above example) is preferred.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product, as illustrated in the examples in the case of the dicyclohexylamine salt.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the

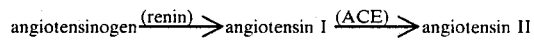

sequence by inhibiting angiotensin converting enzyme and reducing or eliminating the formation of the pressor substance angiotensin II. Thus by the administration of a composition containing one or a combination of compounds of formula I or physiologically acceptable salt thereof, angiotensin dependent hypertension in the species of mammal suffering therefrom is alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, *Proc. Soc. Exp. Biol. Med.* 143, 483 (1973). The substance is preferably administered orally, but parenteral routes such as subcutaneous, intramuscular, intravenous or intraperitoneal can also be employed.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile composition for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, and the like can be incorporated as required.

The present invention will be further described by the following examples. All temperatures are in degrees Celsius unless otherwise indicated. Molar equivalents of the reactants are usually utilized.

Examples 1-15 describe the synthesis of R—A for the various R groups and using several of the A compounds. However, it will be appreciated by those skilled in the art, that other compounds can be made by substituting the desired groups for those used to illustrate the processes where appropriate. Conventional protecting groups are utilized for protecting the side functional groups of the A compounds.

EXAMPLE 1

Synthesis of N$^\alpha$-benzoyl-O-benzyl-threonine

A mixture containing 10 mmoles of O-benzyl-threonine, 10 mmoles of $Na_2CO_3$ in water and tetrahydrofuran (THF) is stirred at room temperature. Benzoyl chloride (10 mmoles), dissolved in anhydrous THF, is added gradually with continued stirring at room temperature. The reaction mixture is stirred until the reaction is completed as judged by thin layer chromatography (TLC). The solvent is removed by a rotary evaporator at 30° C. An excess of water is added and the reaction mixture extracted several times with ethyl acetate. The aqueous phase is adjusted to pH 2 with 1N HCl. The precipitate is recovered by filtration and washed with dilute HCl and then with cold water. The precipitate is dried over $P_2O_5$ in a vacuum desiccator. The precipitate is homogeneous as judged by TLC. In this reaction sequence, the racemate is obtained.

The optical activity can be maintained by reacting molar equivalents of benzoyl chloride and O-benzyl-threonine in a sodium hydroxide solution as described in Carter, H. E., et al., *J. Biol. Chem.* 138, 627 (1941). That is, if O-benzyl-L-threonine or O-benzyl-D-threonine is the starting material, N$^\alpha$-benzoyl-O-benzyl-L-threonine or N$^\alpha$-benzoyl-O-benzyl-D-threonine respectively is produced.

Similarly, if benzoyl N-hydroxysuccinimide ester or other active ester of benzoic acid is used in place of benzoyl chloride in Example 1, the optical activity is maintained.

EXAMPLE 2

By substituting a particular A group or protected A group for O-benzyl-threonine in Example 1 and substantially following the procedure described therein, the N$^\alpha$-benzoyl derivatives of the A compounds are obtained.

EXAMPLE 3

The formyl, acetyl, propanoyl, butanoyl, phenylacetyl, phenylpropanoyl or tert-butyloxycarbonyl (Boc) derivatives of the A compounds are obtained by substituting the appropriate acyl chloride, acyl N-hydroxysuccinimide ester or other acyl active ester for the benzoyl chloride in Examples 1 and 2 and substantially following the procedure of Example 1.

EXAMPLE 4

Synthesis of $N^\alpha$-cyclopentanecarbonyl-4-chloro-phenylalanine

A cool solution of 15 mmoles of dicyclohexylcarbodiimide in dichloromethane is added to a solution of 15 mmoles of cyclopentanecarboxylic acid in dichloromethane at $-5°$ C. 15 mmoles of 4-chloro-phenylalanine t-butyl ester toluenesulfonate salt in dimethylformamide (DMF), which is neutralized with N-ethyl morpholine, is then added. The reaction mixture is stirred at $0°$ C. initially and then at room temperature until the reaction is completed as judged by TLC. Dicyclohexylurea is removed by filtration and 50 ml of ethyl acetate is added to the filtrate. The organic phase is washed until neutral, dried over anhydrous $MgSO_4$ and filtered. The solvent is removed with a rotary evaporator. The residue is crystallized from isopropanol and hexane.

The t-butyl ester is removed by anhydrous HF in the presence of anisole. Solvents are removed by a rotary evaporator. The residue is crystallized from ether and hexane yielding the named compound.

EXAMPLE 5

By substituting a particular A group or protected A group for 4-chlorophenylalanine in Example 4 and substantially following the procedure described therein, the $N^\alpha$-cyclopentanecarbonyl (cpc) derivatives of the A compounds are obtained.

EXAMPLE 6

Synthesis of the N-hydroxysuccinimide ester of cyclopentane carboxylic acid

A cool solution of 20 mmoles of dicyclohexylcarbodiimide in dimethylformamide (DMF) is added drop-wise to a mixture of 20 mmoles of cyclopentanecarboxylic acid and 20 mmoles of N-hydroxysuccinimide in DMF at $0°$ C. The reaction mixture is stirred at $0°$ C. for 30 minutes and then at $4°$ C. overnight. Crystalline dicyclohexylurea is removed by filtration and the precipitate was washed with ethyl acetate. Solvents from the combined filtrates are removed under reduced pressure and the residue is crystallized from benzene and hexane yielding the named product.

EXAMPLE 7

Synthesis of $N^\alpha$-cyclopentanecarbonyl-$N^\epsilon$-tert-butyloxycarbonyl-L-lysine A solution of 10 mmoles of $N^\epsilon$-tert-butyloxycarbonyl-L-lysine and 10 mmoles of $NaHCO_3$ in water and THF is cooled in an ice bath with stirring. To this solution is added a cold solution of 10 mmoles of the product from Example 6 in THF. The THF is removed with a rotary evaporator at $35°$ C. after the reaction mixture is stirred overnight at room temperature. Water is added to the reaction mixture and the pH is adjusted to 9 with solid $NaHCO_3$. The aqueous phase is extracted three times with ethyl acetate and the organic phase is discarded. The aqueous solution is cooled in an ice bath and then acidified to pH 2 with 1N HCl in the presence of ethyl acetate. The organic phase is washed twice with ice water and then twice with a solution of saturated NaCl. The organic solution is dried over anhydrous $MgSO_4$ and then filtered. The solvent is removed with a rotary evaporator and the residue is crystallized from ether and hexane yielding the named product.

EXAMPLE 8

Synthesis of $N^\alpha$-cyclopentanecarbonyl-$N^\epsilon$-tert-butyloxycarbonyl-L-lysine-N-hydroxysuccinimide ester A solution of 10 mmoles of the product from Example 7 and 10 mmoles of N-hydroxysuccinimide in $CH_2Cl_2$ is cooled to $-5°$ C. To this solution is added with stirring a cold solution of 10 mmoles of dicyclohexylcarbodiimide in $CH_2Cl_2$. The reaction mixture is stirred at $0°$ C. for 30 minutes and then at $4°$ C. overnight. Crystalline dicyclohexylurea is removed by filtration and is washed with ethyl acetate. The combined filtrate is washed twice with a 1.0N $NaHCO_3$, twice with water and finally with a solution of saturated NaCl. The organic phase is dried over anhydrous $MgSO_4$, filtered, and the solvent is removed with a rotary evaporator. The residue is crystallized from isopropanol yielding the named product.

EXAMPLE 9

Synthesis and $N^\alpha$-($N^\alpha$-cyclopentanecarbonyl-$N^\epsilon$-tert-butyloxycarbonyl-L-lysyl)-6-methyl-tryptophan A solution of 10 mmoles of the product from Example 8 in dioxane is added dropwise to a mixture of 10 mmoles of 6-methyltryptophan and 10 mmoles of $NaHCO_3$ in a mixture of water and DMF. the reaction mixture is stirred at room temperature overnight and the dioxane is removed with a rotary evaporator at $35°$ C. Ethyl acetate is added to the mixture which is then cooled and acidified to pH 2 with 0.1N HCl. The aqueous phase is discarded. The organic phase is washed with cold water, saturated NaCl and dried over anhydrous $MgSO_4$. The solvent is removed with a rotary evaporator and the residue is crystallized from ether-hexane yielding the named product.

EXAMPLE 10

By substituting a particular A group or protected A group for 6-methyl-tryptophan in Example 9 and substantially following the procedure described therein, the $N^\alpha$-cpc-$N^\epsilon$-Boc-L-Lys derivatives of the A compounds are obtained.

EXAMPLE 11

By substituting pyro-L-glutamic acid for the cyclopentanecarboxylic acid in Example 6 and substantially following the procedures of Examples 6-8, $N^\alpha$-pyro-L-glutamyl-$N^\epsilon$-tert-butyloxycarbonyl-L-lysine-N-hydroxysuccinimide ester is obtained. By substituting this product for the $N^\alpha$-cpc-$N^\epsilon$-Boc-L-Lys-N-hydroxysuccinimide ester in Examples 9 and 10 and substantially following the procedures of Example 9, the $N^\alpha$-pyro-L-glutamyl-$N^\epsilon$-Boc-L-Lys derivatives of the A compounds are obtained.

EXAMPLE 12

Synthesis of N$^\alpha$-pyro-L-glutamyl-phenylglycine benzyl ester

A solution of 20 mmoles of pyro-L-glutamic acid and 20 mmoles phenylglycine benzyl ester toluene sulfonic acid, neutrallized with N-ethyl morpholine, in dichloromethane:DMF (4:1) is cooled in an ice bath with stirring. A solution of 20 mmoles of dicyclohexylcarbodiimide in dichloromethane is added to the above reaction mixture. The reaction mixture is stirred in an ice water bath for 1 hour and then at room temperature overnight. Dicyclohexylurea is removed by filtration and the product is washed in ethyl acetate. Solvents of the combined filtrates are removed under reduced pressure with a rotary evaporator at 40° C. Ethyl acetate is added to the residue and the organic solution is washed until neutral. The organic phase is dried over anhydrous MgSO$_4$, filtered and then the solvent is removed with a rotary evaporator. The material is crystallized from isopropanol and ether yielding the named product.

EXAMPLE 13

Synthesis of N$^\alpha$-pyro-L-glutamyl-phenylglycine

The benzyl ester protecting group of the compound of Example 12 is removed by catalytic hydrogenolysis with 10% palladium on carbon in absolute ethanol. The catalyst is removed by filtration and the ethanol is removed by a rotary evaporator. The residue is crystallized from isopropanol and benzene yielding the named product.

EXAMPLE 14

By substituting N$^\alpha$N, N$^\epsilon$-bis-t-butyloxycarbonyl-L-lysine (hereinafter bis-Boc-L-Lys) or N$^\alpha$, N$^\alpha$, N$^\omega$-triadamantyloxycarbonyl-L-arginine (hereinafter tri-Adoc-L-arginine) for pyro-L-glutamic acid in Example 12 and by following substantially the procedure of Examples 12 and 13, the corresponding bis-Boc-L-Lys or tri-Adoc-L-Arg derivatives of phenylglycine will be synthesized. Bis-Boc-L-Lys is commercially available. Tri-Adoc-L-Arg is prepared according to Jager, G. and Geiger, R., *Chem. Ber.* 102, 1727 (1970).

EXAMPLE 15

By substituting the benzyl esters of a particular A group or protected A group for the phenylglycine in Examples 12 and 14 and substantially following the procedures of Examples 12, 13 and 14, the corresponding pyro-L-glutamyl, bis-Boc-L-Lys and tri-Adoc-L-arg derivatives of the A groups are obtained.

Examples 16–26 describe the synthesis of HS—Z where Z is defined by formula VIII. The procedures followed in these examples are described in U.S. Pat. Nos. 4,046,889 and 4,105,776.

EXAMPLE 16

Synthesis of N-(2-Benzoylthioacetyl)-L-Proline

L-Proline (5.75 g.) is dissolved in 1.0N sodium hydroxide (50 ml.) and the solution is chilled in an ice-water bath. Sodium hydroxide 2N (26 ml.) and chloroacetyl chloride (5.65 g.) are added and the mixture is stirred vigorously at room temperature for 3 hours. A suspension of thiobenzoic acid (7.5 g.) and potassium carbonate (4.8 g.) in water (50 ml.) is added. After 18 hours stirring at room temperature, the reaction mixture is acidified and extracted with ethyl acetate. The ethyl acetate layer is washed with water, dried over magnesium sulfate and concentrated to dryness in vacuo. The residue (14.6 g.) is dissolved in ethyl acetate (150 ml.) and dicyclohexylamine (11 ml.) is added. The crystals are filtered and recrystallized from ethyl acetate, yield 5.7 g. m.p. 151°–152°. To convert the salt to the acid, the crystals are dissolved in a mixture of 5% aqueous potassium bisulfate (100 ml.) and ethyl acetate (300 ml.). The organic phase is washed once with water, dried over magnesium sulfate and concentrated to dryness in vacuo, yield 3.45 g.

EXAMPLE 17

Synthesis of N-(2-Mercaptoacetyl)-L-Proline

N-(2-Benzoylthioacetyl)-L-proline (3.4 g.) is dissolved in a mixture of water (10.5 ml.) and concentrated ammonia (6.4 ml.). After 1 hour, the reaction mixture is diluted with water and filtered. The filtrate is extracted with ethyl acetate and then acidified with concentrated hydrochloric acid, saturated with sodium chloride and extracted twice with ethyl acetate. The ethyl acetate extracts are washed with saturated sodium chloride and concentrated to dryness, yield 1.5 g. The product, N-(2-mercaptoacetyl)-L-proline is crystallized from ethyl acetate (m.p. 133°–135°).

EXAMPLE 18

Synthesis of N-(2-Benzoylthioacetyl)-L-Proline Methyl Ester

N-(2-Benzoylthioacetyl)-L-proline obtained in Example 16, is dissolved in methanol and an ethereal solution of diazomethane is added until there is a persistent yellow color. After 15 minutes, a few drops of acetic acid are added and the solvent is removed in vacuo to obtain N-(2-benzoylthioacetyl)-L-proline methyl ester.

EXAMPLE 19

Synthesis of N-(2-Mercaptoacetyl)-L-Proline Amide

The product of Example 18 is dissolved in 10% methanolic ammonia and the solution is stored at room temperature in a pressure bottle. When thin layer chromatographic analysis indicates that the two ester functions have been ammonolyzed, the reaction mixture is concentrated to dryness to obtain N-(2-mercaptoacetyl)-L-proline amide.

EXAMPLE 20

Synthesis of N-(3-Mercaptopropanoyl)-L-proline tert-butyl Ester

To a solution of L-proline tert-butyl ester (3.42 g.) in dry tetrahydrofuran (10 ml.) chilled in an ice bath, propiothiolacetone (1.76 g.) is added. After 5 minutes storage in the ice bath and 3 hours at room temperature, the reaction mixture is diluted with ethyl acetate (200 ml.) and washed with 5% potassium bisulfate, and water. The organic layer is dried over magnesium sulfate and concentrated to dryness in vacuo. The residue N-(3-mercaptopropanoyl)-L-proline tert-butyl ester is crystallized from ether-hexane, yield 3.7 g., m.p. 57°–58°.

EXAMPLE 21

Synthesis of 3-Acetylthio-2-Methylpropanoic Acid

A mixture of thioacetic acid (50 g.) and methacrylic acid (40.7 g.) is heated on the steam bath for 1 hour and then stored at room temperature for 18 hours. After confirming by nmr spectroscopy that complete reaction of the methacrylic acid has been achieved, the reaction mixture is distilled in vacuo and the desired 3-acetylthio-2-methylpropanoic acid is separated in the fraction with boiling point 128.5°–131° (2.6 mmHg.), yield 64 g.

EXAMPLE 22

Synthesis of N-(3-methylpropanoyl)-L-Proline tert-butyl Ester

L-Proline tert-butyl ester (5.1 g.) is dissolved in dichloromethane (40 ml.) and the solution stirred and chilled in an ice bath. Dicyclohexylcarbodiimide (6.2 g.) dissolved in dichloromethane (15 ml.) is added followed immediately by a solution of 3-acetylthio-2-methylpropanoic acid (4.9 g.) in dichloromethane (5 ml.). After 15 minutes stirring in the ice bath and 16 hours at room temperature, the precipitate is filtered off and the filtrate is concentrated to dryness in vacuo. The residue is dissolved in ethyl acetate and washed neutral. The organic phase is dried over magnesium sulfate and concentrated to dryness in vacuo. The residue, N-(3-acetylthio-2-methylpropanoyl)-L-proline tert-butyl ester, is purified by column chromatography (silica gel, chloroform), yield 7.9 g. The named product is obtained by following the procedure of Example 17.

EXAMPLE 23

Synthesis of N-(3-mercapto-2-D,L-methylpropanoyl)-L-proline

Methacryloyl chloride (4.16 g.) is added to a solution of L-proline (3.45 g.) in a mixture of water (100 ml.) and sodium bicarbonate (12 g.) chilled in an ice water bath, with vigorous stirring. When the addition is completed, the mixture is stirred at room temperature for two hours, and then extracted with ether. The aqueous phase is acidified with 1.0N hydrochloric acid and extracted with ethyl acetate. The organic phase is concentrated to dryness in vacuo, the residue is mixed with thiolacetic acid (3.5 g.), a few crystals of azobisisobutyronitrile are added and the mixture is heated on the steam bath for two hours. The reaction mixture is dissolved in benzene acetic acid (75:25), and applied to a column of silica gel. Elution with the same solvent mixture yields the N-(3-acetylthio-2-D,L-methylpropanoyl)-L-proline. The named product is obtained by following the procedure of Example 17.

EXAMPLE 24

Synthesis of N-[3-(Acetylthio)-2-methylpropanoyl]-D,L-Pipecolic Acid 6.5 g. (0.05 mole) of pipecolic acid are suspended in dimethylacetamide (200 mg.), 9.0 g. (0.05 mole) of 3-acetylthio-2-methylpropanoyl chloride is added dropwise. The temperature rises to 29° and a clear solution forms. Then 10.1 g. of N-methylmorpholine is added all at once and the temperature rises to 34°. The mixture is heated on a steam bath for 1 hour when a clear solution forms. This is allowed to stand at room temperature overnight and the solid which precipitates is filtered to yield 6.1, m.p. 203°–204°. The solvent is removed and the viscous residue is triturated with water and 20% HCl. The yellow oil is extracted with 3×150 ml. of ethyl acetate. The ethyl acetate extracts are dried over magnesium sulfate and removed to yield 14 g. of N-[3-(acetylthio)-2-methylpropanoyl]-D,L-pipecolic acid as a viscous oil.

EXAMPLE 25

Synthesis of N-[3-Mercapto-2-methylpropanoyl]-D,L-Pipecolic Acid

Aqueous NH$_4$OH (30 ml. water and 20 ml. conc. NH$_4$OH) is stirred under nitrogen at 10° for 15 minutes. This is added to 13.0 g. (0.05 m) of N-[3-(acetylthio)-2-methylpropanoyl]-D,L-pipecolic acid and the resulting solution is stirred for 10 minutes under nitrogen; then at room temperature for 50 minutes. It is then treated with water and 20% NaCl and the yellow oil extracted with 3×150 ml. of ethyl acetate. The ethyl acetate extract is dried over magnesium sulfate and removed to yield 11.1 g. N-(3-mercapto-2-methylpropanoyl)-D,L-pipecolic acid as a viscous oil. R$_f$=0.62 [silica gel, benzene, acetic acid (7:2)].

EXAMPLE 26

By substituting the appropriate activated acyl group for the chloroacetyl chloride of Example 16 and by substituting the appropriate amino group for L-Pro of Example 16 and substantially following the procedures of Examples 16–19, the mercapto compounds, HS—Z (VIII), defined in Table 1 are obtained.

TABLE 1

| | $R_{15}$ | $R_{16}$ | $R_{17}$ | $R_{24}$ | r | s |
|---|---|---|---|---|---|---|
| (1) | H | H | H,3-OH | OH | 1 | 2 |
| (2) | H | H | H | OH | 1 | 1 |
| (3) | H | H | H | OH | 1 | 3 |
| (4) | H | H | OH | OH | 1 | 1 |
| (5) | H | $C_2H_5$ | H | OH | 1 | 2 |
| (6) | $CH_3$ | H | Cl | $OC_2H_5$ | 1 | 2 |
| (7) | $CH_3$ | $CH_3$ | H | OH | 1 | 2 |
| (8) | $CH_3$ | $C_6H_5CH_2$ | H | OH | 1 | 2 |
| (9) | $C_2H_5$ | H | H | OH | 1 | 1 |
| (10) | H | $C_4H_9$ | H | OH | 1 | 3 |
| (11) | H | H | H | $NH_2$ | 1 | 2 |
| (12) | H | H | H,3-F | OH | 2 | 2 |
| (13) | H,$CH_3$ | H | H,3-OH | OH | 2 | 2 |
| (14) | $CH_3,CH_3$ | H | H | OH | 2 | 1 |
| (15) | H | $C_2H_5$ | H | OH | 2 | 3 |
| (16) | H,$C_2H_5$ | $CH_3$ | H | $OCH_3$ | 2 | 2 |
| (17) | H | $CH_3$ | H,H,3-OH | $OCH_3$ | 2 | 3 |
| (18) | — | H | H | OH | 0 | 1 |
| (19) | — | H | H,H,4-OH | OH | 0 | 3 |
| (20) | — | $CH_3$ | H | $OC_2H_5$ | 0 | 1 |
| (21) | — | $CH_3$ | H | $NH_2$ | 0 | 3 |
| (22) | — | $C_4H_9$ | H,4-Br | OH | 0 | 2 |
| (23) | — | $CH_3$ | H | OH | 0 | 2 |
| (24) | — | $CH_3$ | OH | OH | 0 | 1 |
| (25) | $C_3H_7$ | H | H | $NH_2$ | 1 | 2 |
| (26) | H | $CH_3$ | H,H,5-OH | OH | 1 | 3 |
| (27) | H | $CH_3$ | H | OH | 2 | 2 |
| (28) | $C_6H_5$—$C_2H_5$ | H | H,4-OH | $OC_3H_7$ | 1 | 2 |
| (29) | $CH_3$ | H | $C_2H_5$ | $NH_2$ | 1 | 1 |
| (30) | H,$C_5H_{11}$ | $CH_3$ | H,3-$C_4H_9$ | OH | 2 | 2 |

Examples 27–29 describe the synthesis of SH—Z where Z is defined by formula XI. The procedures followed in these examples are described in U.S. Pat. No. 4,070,361.

EXAMPLE 27

Synthesis of N-[[2-(Acetylthio)ethyl]sulfonyl]-L-proline a. N-(Vinylsulfonyl)-L-proline t-butyl ester L-Proline t-butyl ester (6.9 g. 0.04 mol.) and triethylamine (14 ml., 0.1 mol.) are dissolved in 200 ml. of dichloromethane and stirred in an ice bath while 2-chloroethanesulfonyl chloride (8.2 g., 0.05 mol.) in 100 ml. of dichloromethane is added over 20 minutes. After stirring 2 hours, the mixture is washed with 5% potassium bisulfate solution, saturated sodium bicarbonate solution and brine, then evaporated in vacuo. The semi-solid residue is chromatographed on 350 ml. silica gel using 1:1 ethyl acetate/hexane as eluant. The main fraction, comprising N-(vinylsulfonyl)-L-proline t-butyl ester is crystallized from ether/hexane, m.p. 84°–87° (7.1 g., 68%).

b. N-[[2-(Acetylthio)ethyl]sulfonyl]-L-proline t-butyl ester

N-(Vinylsulfonyl)-L-proline t-butyl ester (5.0 g., 0.0192 mol.), triethylamine (2.8 ml., 0.02 mol.) and thiolacetic acid (1.43 ml., 0.02 mol.) are mixed in 100 ml. of ether and allowed to stand overnight. The mixture is washed with 5% potassium bisulfate solution, saturated sodium bicarbonate solution and brine, then evaporated in vacuo to a yellow oil. The procedure is repeated using half of the above quantities of triethylamine and thiolacetic acid. Workup as in part (a) affords the crude product, N-[[2-(acetylthio)ethyl]sulfonyl]-L-proline t-butyl ester, which is filtered through a short silica gel column and crystallized from ether/hexane, m.p. 46°–50° (2.9 g., 45%).

c. N-[[2-(Acetylthio)ethyl]sulfonyl]-L-proline

The t-butyl ester from part (b) (2.9 g., 0.0086 mol.) is dissolved in 15 ml. of anisole and 45 ml. of trifluoroacetic acid and let stand 1 hour. The mixture is evaporated in vacuo to a gummy residue which is taken up in ethyl acetate and treated with a large volume of hexane. The supernatant is decanted, and the procedure repeated. The resulting semisolid is crystallized from ethyl acetate-hexane, m.p. 63°–67°.

EXAMPLE 28

Synthesis of N-[(2-Mercaptoethyl)sulfonyl]-L-proline

N-[[2-(Acetylthio)ethyl]sulfonyl]-L-proline (640 mg., 0.0023 mol.) is dissolved in 5 ml. of water and 5 ml. of concentrated ammonia and stirred 1 hour under nitrogen. The solution is acidified with concentrated hydrochloric acid, extracted with ethyl acetate, and the extracts are washed with brine, dried (MgSO4) and evaporated to an oily residue which is applied to a 75 ml. silica gel column. Elution with 10% acetic acid/benzene affords a main fraction which is crystallized from chloroform/hexane, to obtain 440 mg. (81%) of 1-[(2-mercaptoethyl)sulfonyl]-L-proline, m.p. 99°–101°.

EXAMPLE 29

By substituting the appropriate haloalkylsulfonyl halide for the 2-chloroethanesulfonyl chloride of Example 27 and by substituting the appropriate amino group for the L-Pro-t-butyl ester of Example 27 and substantially following the procedures of Examples 27–28, the mercapto compounds, HS—Z (XI), defined in Table 2 are obtained.

TABLE 2

| | $R_{10}$ | $R_{23}$ | z |
|---|---|---|---|
| (1) | $CH_3$ | H | 2 |
| (2) | H | $CH_3$ | 2 |
| (3) | $C_3H_7$ | H | 2 |
| (4) | $C_2H_5$ | $C_2H_5$ | 2 |
| (5) | $C_4H_9$ | H | 2 |
| (6) | H | H | 3 |
| (7) | $CH_3$ | $C_5H_{11}$ | 3 |
| (8) | $CH_3$ | H | 3 |
| (9) | $C_4H_9$ | $CH_3$ | 3 |
| (10) | $CH_3$ | $CH_3$ | 3 |

Examples 30–35 describe the synthesis of HS—Z where Z is defined by formula II. The procedures followed in these examples are described in U.S. Pat. No. 4,154,935.

EXAMPLE 30

Synthesis of 3-Acetylthio-2-trifluoromethylpropanoic acid

A mixture of thiolactic acid (50 g.) and 2-(trifluoromethyl)acrylic acid [M. W. Buxton, et al., *J. Chem. Soc.*, 366 (1954)] (66 g.) is heated on the steam bath for one hour and then stored at room temperature for eighteen hours. The reaction mixture is distilled in vacuo to give 3-acetylthio-2-trifluoromethylpropanoic acid.

EXAMPLE 31

Synthesis of N-(3-Acetylthio-2-trifluoromethylpropanoyl)-L-proline tert-butyl ester L-proline tert-butyl ester (5.1 g.) is dissolved in dichloromethane (40 ml.) and the solution is stirred and chilled in an ice bath. Dicyclohexylcarbodiimide (6.2 g.) dissolved in dichloromethane (15 ml.) is added followed immediately by a solution of 3-acetylthio-2-trifluoromethylpropanoic acid (6.5 g.) in dichloromethane (5 ml.). After fifteen minutes stirring in the ice bath and sixteen hours at room temperature, the precipitate formed is filtered off and the filtrate is concentrated to dryness in vacuo. The residue is dissolved in ethyl acetate and washed neutral. The organic phase is dried over magnesium sulfate and concentrated to dryness in vacuo to give N-(3-acetylthio-2-trifluoromethylpropanoyl)-L-proline tert-butyl ester.

EXAMPLE 32

Synthesis of N-(3-Acetylthio-2-trifluoromethylpropanoyl)-L-proline

N-(3-Acetylthio-2-trifluoromethylpropanoyl)-L-proline tert-butyl ester (8 g.) is dissolved in a mixture of anisole (55 ml.) and trifluoroacetic acid (110 ml.). After one hour storage at room temperature the solvent is removed in vacuo and the residue is precipitated several times from ether-hexane to give N-(3-acetylthio-2-trifluoromethylpropanoyl)-L-proline.

EXAMPLE 33

Synthesis of N-(3-Mercapto-2-trifluoromethylpropanoyl)-L-proline

N-(3-Acetylthio-2-trifluoromethylpropanoyl)-L-proline (4 g.) is dissolved in a mixture of water (8 ml.) and concentrated ammonia (8 ml.) under a blanket of nitrogen. After twenty-five minutes stirring at room temperature, the reaction mixture is chilled, acidified and extracted with ethyl acetate. The organic layer is concentrated to dryness in vacuo to yield N-(3-mercapto-2-trifluoromethylpropanoyl)-L-proline.

EXAMPLE 34

Synthesis of N-(2-mercapto-3,3,3-trifluoropropanoyl)-L-proline

To a solution of L-proline (5.75 g.) in 1N sodium hydroxide (50 ml.), chilled in an ice-water bath, 2-bromo-3,3,3-trifluoropropanoic acid chloride (12 g.) is added and the mixture is vigorously stirred at room temperature for three hours. A solution of thiolacetic acid (4 ml.) and potassium carbonate (4.8 g.) in water (50 ml.) is added and the mixture is stirred at room temperature for sixteen hours. After extraction with ethyl acetate, the aqueous layer is acidified with concentrated hydrochloric acid and extracted again with ethyl acetate. This last organic phase is dried over magnesium sulfate and concentrated to dryness in vacuo. The residue is chromatographed on a silica gel column with a mixture of benzene-acetic acid (7:2) to yield N-(2-acetylthio-3,3,3-trifluoropropanoyl)-L-proline. The named product is obtained by following the procedure of Example 33.

EXAMPLE 35

By substituting the appropriate activated acyl group for the 2-bromo-3,3,3-trifluoropropanoic acid chloride in Example 34 or by substituting the appropriate thioacyl group for the 3-acetylthio-2-trifluoromethyl-propanoic acid in Example 31 and by substituting the appropriate amino group for the L-Pro of Example 34 or for the L-Pro-t-butyl ester of Example 31 and substantially following the procedures of Example 34 or Examples 31–33, the mercapto compounds, HS—Z (II), defined in Table 3 are obtained.

TABLE 3

|      | $R_2$    | $R_3$    | $R_1$ | $R_1'$ | $R_{23}$ | m |
|------|----------|----------|-------|--------|----------|---|
| (1)  | —        | H        | F     | F      | H        | 0 |
| (2)  | —        | F        | F     | F      | $C_2H_5$ | 0 |
| (3)  | —        | $CF_3$   | F     | H      | H        | 0 |
| (4)  | —        | $C_2H_5$ | F     | F      | $CH_3$   | 0 |
| (5)  | —        | $CH_3$   | F     | H      | H        | 0 |
| (6)  | —        | $C_4H_9$ | F     | F      | H        | 0 |
| (7)  | —        | $CF_3$   | F     | H      | $C_3H_7$ | 0 |
| (8)  | $CF_3$   | H        | H     | F      | H        | 1 |
| (9)  | $CF_3$   | $C_3H_7$ | F     | F      | $CH_3$   | 1 |
| (10) | $C_2H_5$ | $CH_3$   | F     | F      | H        | 1 |
| (11) | H        | H        | F     | F      | H        | 1 |
| (12) | $CF_3$   | H        | H     | H      | $C_4H_9$ | 1 |
| (13) | $C_5H_{11}$ | $CF_3$ | F     | H      | H        | 1 |
| (14) | H        | $CH_3$   | F     | H      | H        | 1 |
| (15) | $CH_3$   | $C_2H_5$ | F     | H      | $CH_3$   | 1 |

Examples 36–40 describe the synthesis of HS—Z where Z is defined by formula III. The procedures followed in these examples are described in U.S. Pat. No. 4,154,934.

EXAMPLE 36

Synthesis of N-nitroso-L-proline

To a cooled suspension of 28.2 g. of nitrosyl tetrafluoroborate in 300 ml. of dry acetonitrile there is added, with vigorous stirring, over the course of 10 minutes, 18.4 g. of L-proline, followed by a solution of 19 g. of pyridine is 50 ml. of acetonitrile during 15 minutes. The stirring is continued for an hour and the reaction mixture is then concentrated to dryness under reduced pressure. The residue is extracted with 3×200 ml. of ethyl acetate, the ethyl acetate extracts are combined, washed twice with saturated sodium chloride solution that has been made slightly acidic with concentrated hydrochloric acid. The ethyl acetate solution is dried over anhydrous sodium sulfate, filtered and concentrated to dryness at room temperature under reduced pressure. The product, N-nitroso-L-proline melts at 108°–109° (dec.) after crystallization from a mixture of ether and petroleum ether (30°–60°).

EXAMPLE 37

Synthesis of N-amino-L-proline

A solution of 10 g. of N-nitroso-L-proline in 500 ml. of 50% acetic acid is cooled in an ice bath and 40 g. of zinc dust is added gradually, with vigorous stirring, at a rate that the temperature of the reaction mixture is maintained below 10°. The addition requires about 15 minutes. The unreacted zinc dust is removed by filtration and the filtrate treated with hydrogen sulfide to precipitate the zinc as zinc sulfide. The precipitated zinc sulfide is removed by filtration and the filtrate evaporated to dryness. The residue is dissolved in 30 ml. of absolute ethanol and the solution allowed to remain overnight at 5°. The N-amino-L-proline, a yellow crystalline solid is removed by filtration and melts at 153°–154° after drying.

EXAMPLE 38

Synthesis of N-[[3-(Acetylmercapto)-1-oxopropyl]amino]-L-proline

To a suspension of 3.9 g. of N-amino-L-proline and 6.06 g. of N-methylmorpholine in 200 ml. of dimethylacetamide is added 4.98 g. of 3-acetylthiopropionyl chloride. The temperature of the reaction mixture rises to 34° spontaneously. The reaction mixture is then heated at 90° for 5 hours and allowed to cool to room temperature overnight. The crystalline solid, N-methylmorpholine hydrochloride, is removed by filtration and the filtrate concentrated under reduced pressure. The residue is dissolved in a minimum amount of 20% hydrochloric acid and the aqueous solution is then extracted with 3×150 ml. of ethyl acetate. The ethyl acetate extracts are combined, dried over anhydrous magnesium sulfate, and then concentrated under reduced pressure to yield the desired N-[[3-(acetylmercapto)-1-oxopropyl]amino]-L-proline.

EXAMPLE 39

Synthesis of N-[(3-Mercapto-1-oxopropyl)amino]-L-proline

Nitrogen is bubbled into a solution of 12 ml. of concentrated aqueous ammonia in 25 ml. of water at 10° for 15 minutes. To this solution there is added 5.8 g. of N-[[3-acetylmercapto)-1-oxopropyl]amino]-L-proline and the resulting solution is stirred for 2½ hours under nitrogen. It is then cooled in an ice-bath and made strongly acidic with 20% hydrochloric acid. The mixture is extracted with 3×150 ml. of ethyl acetate, the ethyl acetate extracts are dried over anhydrous magnesium sulfate and then concentrated under reduced pressure. The oily residue is triturated with ether, the ether decanted and the last traces of ether removed under reduced pressure. The oily residue is dissolved in water and lyophilized to yield N-[(3-mercapto-1-oxopropyl)amino]-L-proline hemihydrate as a viscous oil.

Analysis calcd. for $C_8H_{14}N_2O_3S.\frac{1}{2}H_2O$: C, 42.27; H, 6.65; N, 12.32; S, 14.11 Found: C, 42.59; H, 6.68; N, 12.29; S, 14.29.

EXAMPLE 40

By substituting the appropriate starting materials into Examples 36-39 and substantially following the procedures of Examples 36-39, the mercapto compounds HS—Z (III), defined in Table 4 are obtained.

TABLE 4

| | $R_4$ | $R_5$ | $R_6$ | $R_{23}$ | m | n |
|---|---|---|---|---|---|---|
| (1) | — | $C_2H_5$ | H | H | 0 | 1 |
| (2) | — | $CH_3$ | OH | $CH_3$ | 0 | 1 |
| (3) | — | H | H | $C_3H_7$ | 0 | 1 |
| (4) | — | H | H | H | 0 | 2 |
| (5) | — | $CH_3$ | H,3-OH | H | 0 | 2 |
| (6) | — | H | H,4-OH | $CH_3$ | 0 | 2 |
| (7) | — | $C_6H_5CH_2$ | H | H | 0 | 2 |
| (8) | — | H | H | $C_4H_9$ | 0 | 3 |
| (9) | — | $C_3H_7$ | H,H,5-OH | H | 0 | 3 |
| (10) | H | H | H | H | 1 | 1 |
| (11) | H | H | OH | $CH_3$ | 1 | 1 |
| (12) | $C_2H_5$ | $CH_3$ | H | H | 1 | 1 |
| (13) | H | $CH_3$ | H,3-I | H | 1 | 2 |
| (14) | H | H | H,3-OH | $C_2H_5$ | 1 | 2 |
| (15) | $C_2H_5$ | $C_2H_5$ | H | H | 1 | 2 |
| (16) | $C_6H_5CH_2CH_2$ | H | H,4-OH | $CH_3$ | 1 | 2 |
| (17) | $CH_3$ | H | H | H | 1 | 3 |
| (18) | H | H | H,H,3-OH | $C_3H_7$ | 1 | 3 |
| (19) | H | $C_4H_9$ | H,H,4-OH | H | 1 | 3 |
| (20) | $CH_3$ | $C_2H_5$ | H | H | 1 | 3 |

Examples 41-44 describe the synthesis of HS—Z where Z is defined by formula X. The procedures followed in these examples are described in U.S. Pat. No. 4,129,566.

EXAMPLE 41

Synthesis of N-(3-Acetylthio-2-ethylpropanoyl)-L-3,4-dehydroproline

L-3,4-dehydroproline (3.4 g.) is dissolved in 1.0N sodium hydroxide (30 ml.) and the solution is chilled in an ice-water bath. 3-Acetylthio-2-ethylpropanoyl chloride (5.84 g.) and 2N sodium hydroxide (15 ml.) are added and the solution is stirred at room temperature for 3 hours. The mixture is extracted with ether, acidified and extracted with ethyl acetate. The organic phase is dried over magnesium sulfate and evaporated to dryness to yield N-(3-acetylthio-2-ethylpropanoyl)-L-3,4-dehydroproline.

EXAMPLE 42

Synthesis of N-(2-Ethyl-3-mercaptopropanoyl)-L-3,4-dehydroproline

N-(3-Acetylthio-2-ethylpropanoyl)-L-3,4-dehydroproline (3 g.) is dissolved in a mixture of water (10 ml.) and concentrated ammonia (10 ml.) under a blanket of nitrogen. After 25 minutes, the reaction mixture is acidified and extracted with ethyl acetate. The organic layer is dried over magnesium sulfate and evaporated to dryness to yield N-(2-ethyl-3-mercaptopropanoyl)-L-3,4-dehydroproline.

EXAMPLE 43

Synthesis of N-(2-mercaptopropanoyl)-D,L-4,5-dehydropiperidine-2-carboxylic acid D,L-4,5-dehydropiperidine-2-carboxylic acid (5.65 g.) is dissolved in 1.0N aqueous sodium hydroxide (50 ml.) and the solution is chilled in an ice-water bath with stirring. 2N Sodium hydroxide (25 ml.) and 2-bromopropanoyl chloride (8.57 g.) are added. The mixture is stirred at room temperature for one hour. A mixture of thioacetic acid (4.18 g.) and potassium carbonate (4.8 g.) in water (50 ml.) is added and the mixture is stirred at room temperature for eighteen hours. After acidification, the mixture is extracted with ethyl acetate. The organic layer is dried over magnesium sulfate and concentrated to dryness in vacuo to yield N-(2-acetylthiopropanoyl)-D,L-4,5-dehydropiperidine-2-carboxylic acid. The named product is obtained by following the procedure of Example 42.

EXAMPLE 44

By substituting the appropriate starting materials into Examples 41 or 43 and substantially following the procedures of Examples 41-43, the mercapto compounds, HS—Z (X), defined in Table 5 are obtained.

TABLE 5

| | $R_{22}$ | $R_{23}$ | $R_{26}$ | t | u |
|---|---|---|---|---|---|
| (1) | H | $C_2H_5$ | O=⟨N–COOR$_{23}$⟩ (5-oxo pyrrolidine) | 0 | — |
| (2) | $CH_3$ | H | dehydropiperidine-$(CH_2)_u$–COOR$_{23}$ | 0 | 0 |
| (3) | H | H | thiazolidine-COOR$_{23}$ | 0 | — |
| (4) | $C_3H_7$ | H | dehydropiperidine-$(CH_2)_u$–COOR$_{23}$ | 0 | 1 |
| (5) | H | $C_4H_4$ | dehydropiperidine-$(CH_2)_u$–COOR$_{23}$ | 0 | 1 |
| (6) | $CH_3$ | $C_3H_7$ | thiazolidine-COOR$_{23}$ | 1 | — |
| (7) | $C_5H_{11}$ | H | 5-oxo pyrrolidine-COOR$_{23}$ | 1 | — |
| (8) | H | $CH_3$ | dehydropiperidine-$(CH_2)_u$–COOR$_{23}$ | 1 | 0 |

TABLE 5-continued

| | $R_{22}$ | $R_{23}$ | $R_{26}$ | t | u |
|---|---|---|---|---|---|
| (9) | $CH_3$ | H | (tetrahydropyridine ring with N, $(CH_2)_u$, $COOR_{23}$) | 1 | 1 |
| (10) | $C_2H_5$ | H | (oxo-pyrrolidine ring with N, $COOR_{23}$) | 1 | — |
| (11) | $CH_3$ | $CH_3$ | (thiazolidine ring with S, N, $COOR_{23}$) | 0 | — |

Examples 45–48 describe the synthesis of HS—Z where Z is defined by formula IX. The procedures followed in these examples are described in U.S. Pat. No. 4,108,886.

EXAMPLE 45

Synthesis of 2-[(3-Benzoylthiopropanoyl)amino]-2-methylpropanoic acid

α-Aminoisobutyric acid (5.15 g.) is dissolved in 59 ml. of 0.85N sodium hydroxide while stirring in an ice bath. To this, 25 ml. of 2N sodium hydroxide is added, followed by 8.5 g. of 3-bromopropionyl chloride. The bath is removed, and the pH adjusted to 7.3 with 2N sodium hydroxide. After 2 hours, a solution of 7.5 g. of thiobenzoic acid and 4.8 g. of potassium carbonate in 50 ml. of water is added. The reaction mixture is stirred overnight at room temperature, acidified with concentrated hydrochloric acid and extracted with ethyl acetate. The organic layer is dried and concentrated to dryness, yield 13.1 g. The product, 2-[(3-benzoylthiopropanoyl)amino]-2-methylpropanoic acid, is crystallized from ethylacetate-ether, yield 5.4 g., m.p. 142°–143°.

EXAMPLE 46

Synthesis of 2-[(3-Mercaptopropanoyl)amino]-2-methylpropanoic acid 2.8 g. of the product of Example 45 is treated with a mixture of 20 ml. water and 20 ml. of concentrated ammonium hydroxide solution under an argon blanket for one hour. The benzamide precipitate is filtered and the filtrate is extracted twice with ethyl acetate. The aqueous phase is concentrated in vacuo, acidified with concentrated hydrochloric acid and extracted with ethyl acetate. The organic layer is dried and concentrated to dryness in vacuo and the residual product 2-[(3-mercaptopropanoyl)amino]-2-methylpropanoic acid, is crystallized from acetonitrile, yield 1.2 g., m.p. 169°–170°.

EXAMPLE 47

Synthesis of 1-[(3-mercaptopropanoyl)amino]cyclopentane carboxylic acid

1-Aminocyclopentane-1-carboxylic acid (6.45 g.) is dissolved in 50 ml. of 1N sodium hydroxide solution and stirred in an ice bath. To this 25 ml. of 2N sodium hydroxide solution is added, followed immediately with 8.5 g. of 3-bromopropionyl chloride. The bath is removed and the pH is about 7. Some crystals come out of solution. After 3.5 hours at room temperature, 54 ml. of 1N sodium hydroxide solution is added and everything goes into solution. This is followed immediately with 4.12 g. of thiolacetic acid. An additional 5 ml. of 1N sodium hydroxide is added to bring the pH to near 8. After standing overnight, the mixture is acidified with concentrated hydrochloric acid, extracted with ethyl acetate, dried over magnesium sulfate, and concentrated to dryness in vacuo. The product, 1-[3-acetylthiopropanoyl)amino]cyclopentane carboxylic acid, is first crystallized from ethyl acetate and hexane. This material is recrystallized from ethyl acetate, yield 3.655 g., m.p. 127°–128°. The named product is obtained by following the procedure of Example 46.

EXAMPLE 48

By substituting the appropriate starting materials into Example 45 and substantially following the procedures of Example 45 and 46, the mercapto compounds, HS—Z(IX), defined in Table 6 are obtained.

TABLE 6

| | $R_{18}$ | $R_{19}$ | $R_{20}$ | $R_{21}$ | methylene bridge $R_{19-20}$ | $R_{19-21}$ |
|---|---|---|---|---|---|---|
| (1) | $CH_3$ | $C_2H_5$ | $CH_3$ | H | — | — |
| (2) | H | $CH_3$ | $C_4H_9$ | $CH_3$ | — | — |
| (3) | $C_3H_7$ | $CH_3$ | $C_2H_5$ | $C_2H_5$ | — | — |
| (4) | $CH_3$ | — | — | H | $(CH_2)_4$ | — |
| (5) | H | — | — | $C_3H_7$ | $(CH_2)_4$ | — |
| (6) | $C_5H_{11}$ | — | — | $CH_3$ | $(CH_2)_4$ | — |
| (7) | $CH_3$ | — | H | — | — | $(CH_2)_3$ |
| (8) | $C_4H_9$ | — | H | — | — | $(CH_2)_3$ |
| (9) | H | — | $CH_3$ | — | — | $(CH_2)_3$ |
| (10) | $C_2H_5$ | — | $C_3H_7$ | — | — | $(CH_2)_3$ |

Examples 49–52 describe the synthesis of HS—Z where Z is defined by formula VII. The procedures followed in these examples are described in U.S. Pat. No. 4,053,651.

EXAMPLE 49

Synthesis of N-(3-Benzoylthiopropanoyl)-L-alanine

L-alanine (4.45 g.) is dissolved in aqueous 1.0N sodium hydroxide (50 ml.) and the solution is chilled in the ice bath with stirring. 2N sodium hydroxide (27 ml.) and 3-bromopropionyl chloride (8.5 g.) are added in that order and the mixture is removed from the ice bath and stirred at room temperature for three and one half hours. A mixture of thiobenzoic acid (7.5 g.) and potassium carbonate (4.8 g.) in water (50 ml.) is added and the mixture is stirred at room temperature overnight. After acidification with concentrated hydrochloric acid the aqueous solution is extracted with ethyl acetate, and the organic phase is washed with water, dried and concentrated to dryness. The residue (14.9) is crystallized from ether to yield 7.1 g. of N-(3-benzoylthiopropanoyl)-L-alanine, m.p. 99°–100°.

EXAMPLE 50

Synthesis of N-(3-mercaptopropanoyl)-L-alanine

N-(3-benzoylthiopropanoyl)-L-alanine (4.2 g.) is dissolved in a mixture of water (7.5 ml.) and concentrated ammonium hdroxide (6 ml). After one hour, the mixture is diluted with water, filtered and the filtrate is extracted with ethyl acetate. The aqueous phase is acidified with concentrated hydrochloric acid and extracted with

EXAMPLE 55

Synthesis of N-Acetyl-D,L-cysteinyl-L-proline

N,S-Diacetyl-D,L-cysteinyl-L-proline (0.3 g.) is dissolved in a mixture of water (4 ml.) and concentrated ammonia (4 ml.) under a blanket of argon. The solution is stored for thirty minutes at room temperature, saturated with sodium chloride and extracted with ethyl acetate and chloroform. The organic layers are pooled and concentrated to dryness in vacuo to obtain N-acetyl-D,L-cysteinyl-L-proline, yield 0.1 g., $R_f$=0.25 (silica gel; benzene:acetic acid, 75:25).

EXAMPLE 56

Synthesis of N-acetyl-3-acetylthiovalyl-L-proline t-butyl ester

By substituting N,S-diacetyl-penicillamine for the N,S-diacetyl-D,L-cysteine in the procedure of Example 53, N-acetyl-3-acetylthiovalyl-L-proline t-butyl ester is obtained.

EXAMPLE 57

Synthesis of N-acetyl-3-mercaptovalyl-L-proline

By substituting the product of Example 56 for the N,S-diacetyl-D,L-cysteinyl-L-proline t-butyl ester in the procedure of Examples 54 and 55, the named product is obtained.

EXAMPLE 58

Synthesis of Methyl N-(p-methoxybenzyl)nipecotate hydrochloride

A mixture of 23 g. of methyl nipecotate, 24.3 g. of potassium carbonate, and 52 g. of p-methoxybenzyl trichloroacetate in 800 ml. of toluene is refluxed under nitrogen for seventy-two hours. The mixture is cooled, the toluene removed in vacuo, the residue dissolved in chloroform, and this solution washed once with 400 ml. of aqueous potassium carbonate and then with 400 ml. of 10% hydrochloric acid. The chloroform solution is dried and concentrated in vacuo to a viscous brown oil. Trituration of this oil with ethyl acetate affords 30.7 g. of methyl N-(p-methoxybenzyl)nipecotate hydrochloride as an off-white crystalline solid. Recrystallization from ethyl acetate yields the analytical sample, m.p. 150°–154°.

EXAMPLE 59

Synthesis of N-(p-Methoxybenzyl)-3-methylene-2-piperidone

A solution of methyl N-(p-methoxybenzoyl)nipecotate hydrochloride (30.7 g.) and 8.4 g. of sodium hydroxide in 900 ml. of methanol and 45 ml. of water is stirred at room temperature for seventeen hours. The solution is evaporated to dryness in vacuo, the residue diluted with toluene, and this again evaporated to dryness in vacuo. To the residue is added 1 liter of acetic anhydride and 140 ml. of triethylamine, and the resulting mixture is heated under reflux for four hours. The reaction mixture is evaporated to dryness in vacuo, the residue taken up in chloroform, washed with water, dried and concentrated in vacuo. The residual oil is chromatographed on silica gel using 1:1 hexane-ethyl acetate as the eluant, and yields 16.9 g. of N-(p-methoxybenzyl)-3-methylene-2-piperidone as a chromatographically pure yellow oil. Alternatively, the oil can be distilled to give analytically pure N-(p-methoxybenzyl)-3-methylene-2-piperidone, b.p. 145°–155°/0.05 mm.

EXAMPLE 60

Synthesis of 3-Methylene-2-piperidone

A solution of N-(p-methoxybenzyl)-3-methylene-2-piperidone (16.9 g.) and 21.3 g. of anisole in 400 ml. of trifluoroacetic acid is refluxed under nitrogen for forty-eight hours. The solution is evaporated to dryness in vacuo, and the residue chromatographed on 900 g. of silica gel using ethyl acetate as eluant, yielding 6.5 g. of 3-methylene-2-piperidone as a crystalline solid.

EXAMPLE 61

Synthesis of 2-Methylene-5-aminopentanoic acid hydrochloride

A solution of 2.6 g. of 3-methylene-2-piperidone in 150 ml. of 6N hydrochloric acid is refluxed for twenty-four hours. The cooled solution is extracted with chloroform, and the aqueous layer concentrated in vacuo to 3.8 g. of glassy foam. The foam is heated with methanol, filtered through Celite (diatomaceous earth clarifying agent) to remove a small amount of insoluble material, and the filtrate is evaporated to dryness in vacuo, yielding 2.5 g. of 2-methylene-5-aminopentanoic acid hydrochloride as a tan crystalline solid. Recrystallation from isopropanol gives the analytical sample, m.p. 138°–144°.

EXAMPLE 62

Synthesis of 2-Methylene-5-(p-methoxybenzyloxycarbonyl)aminopentanoic acid

To a solution of 8.8 g. of 2-methylene-5-aminopentanoic acid hydrochloride in 100 ml. of water is added with stirring 6.36 g. of magnesium oxide, followed by a solution of 12.2 g. of p-methoxybenzyloxycarbonyl azide in 100 ml. of dioxane, and the resulting mixture is stirred at room temperature for two days. The reaction mixture is filtered, and the filtrate diluted with 200 ml. of ethyl acetate, two equivalents of Dowex 50 ion exchange resin is added, and the mixture is stirred at room temperature for two hours. The resin is then filtered off and washed with water. The layers in the filtrate are separated and the aqueous layer is extracted twice with ethyl acetate. The combined organic layers are dried and concentrated in vacuo to give 18.2 g of 2-methylene-5-(p-methoxybenzyloxycarbonyl)aminopentanoic acid as an amber oil which crystallizes on standing. This is used without further purification.

EXAMPLE 63

Synthesis of 2-Acetylthiomethyl-5-(p-methoxybenzyloxycarbonyl)amino pentanoic acid A solution of 2-methylene-5-(p-methoxybenzyloxycarbonyl)amino pentanoic acid (53 mmoles) in 50 ml. of thiolacetic acid is allowed to stand at room temperature for forty-eight hours. The solution is evaporated to dryness in vacuo, and the residue taken up in chloroform and applied to a silica gel column (700 g.). Elution with 5% methanol in chloroform affords 14.2 g. of 2-acetylthiomethyl-5-(p-methoxybenzyloxycarbonyl)aminopentanoic acid as an oil. Treatment of this oil with one equivalent of dicyclohexylamine in ether, followed by recrystallization from ethyl acetate affords ethyl acetate. The organic phase is washed with water, dried and concentrated to dryness in vacuo. The residue is crystallized from ethyl acetate-hexane to yield 1.87 g. of N-(3-mercaptopropanoyl)-L-alanine, m.p. 79°–81°.

EXAMPLE 51

Synthesis of N-(3-mercapto-2-methylpropanoyl)-L-valine

L-valine (88 g.) and sodium carbonate (40 g.) are dissolved in water (1 l.) and the solution is chilled in an ice bath with vigorous stirring. 3-Acetylthio-2-methylpropanoyl chloride (135 g.) and a solution of sodium carbonate (120 g.) in 500 ml. of water are added in five equal portions over a 15 minute period. After 1.5 hours the reaction mixture is extracted with ethyl acetate, the aqueous phase is acidified with concentrated hydrochloric acid and extracted with ethyl acetate. The organic phase is washed with water, dried over magnesium sulfate and concentrated to dryness to yield 190 g. of N-(3-acetylthio-2-methylpropanoyl)-L-valine. The named product is obtained by following the procedure of Example 50.

EXAMPLE 52

By substituting the appropriate starting materials into Examples 49 or 51 and substantially following the procedures of Examples 49–51, the mercapto compounds, HS—Z (VII), defined in Table 7 are obtained.

followed in these examples are described in U.S. Pat. Nos. 4,113,715 and 4,146,611.

EXAMPLE 53

Synthesis of N,S-Diacetyl-D,L-cysteinyl-L-proline tert-butyl ester

To a solution of L-proline tert-butyl ester (0.85 g.) and hydroxybenzotriazole (0.67 g.) in methylene chloride (10 ml.) chilled in an ice bath, dicyclohexylcarbodiimide (1.03 g.) and N,S-diacetyl-D,L-cysteine (1.7 g.) are added in that order. After fifteen minutes, the ice bath is removed and the mixture is stirred at room temperature overnight. The precipitate is filtered off and the filtrate is washed with 10% potassium bisulfate, water, saturated sodium bicarbonate, and water. The organic phase is dried and concentrated to dryness in vacuo to give N,S-diacetyl-D,L-cysteinyl-L-proline tert-butyl ester as an oil. $R_f=0.25$ (silica gel, ethylacetate).

EXAMPLE 54

Synthesis of N,S-Diacetyl-D,L-cysteinyl-L-proline

N,S-Diacetyl-D,L-cysteinyl-L-proline tert-butyl ester (1.9 g.) is dissolved in a mixture of anisole (6 ml.) and trifluoroacetic acid (12 ml.) and the solution is stored at room temperature for one hour, The solvents are removed in vacuo and the residue is precipitated from ethyl acetate-ether-hexane, to obtain N,S-diacetyl-

TABLE 7

| | $R_4$ | $R_5$ | $R_{13}$ | $R_{14}$ | q |
|---|---|---|---|---|---|
| (1) | — | H | H | —$(CH_2)_4$—$NH_2$ | 0 |
| (2) | — | H | H | —$(CH_2)_3$—NH—$\overset{\overset{\displaystyle NH}{\|}}{C}$—$NH_2$ | 0 |
| (3) | — | $CH_3$ | H | —$CH_2CO_2H$ | 0 |
| (4) | — | H | $CH_3$ | —$CH_2CH(CH_3)_2$ | 0 |
| (5) | — | $C_2H_5$ | $CH_3$ | $C_6H_5CH_2$ | 0 |
| (6) | H | $C_6H_5CH_2$ | H | H | 1 |
| (7) | $CH_3$ | H | H | $CH_2OH$ | 1 |
| (8) | $C_4H_9$ | $CH_3$ | H | 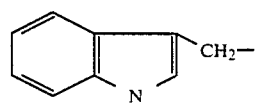 | 1 |
| (9) | H | H | $C_2H_5$ | $CH_3$—S—$CH_2CH_2$— | 1 |
| (10) | $CH_3$, H | H | $CH_3$ | H | 2 |
| (11) | H, $C_6H_5CH_2CH_2$ | $CH_3$ | H | —$CH_2\overset{\overset{\displaystyle O}{\|}}{C}$—$NH_2$ | 2 |
| (12) | H | $C_5H_{11}$ | H | 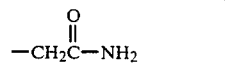 | 2 |
| (13) | H | H | H | —$CH_2SH$ | 2 |
| (14) | H, $CH_3$ | H | $C_3H_7$ | $CH_3$ | 2 |
| (15) | H | $C_3H_7$ | H | 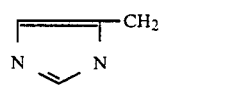 | 1 |
| (16) | $CH_3$ | $C_2H_5$ | $C_6H_5CH_2$ | —$CH(CH_3)(C_2H_5)$ | 1 |

Examples 53–68 describe the synthesis of HS—Z where Z is defined by formula IV. The procedures D,L-cysteinyl-L-proline, yield 1.08 g., m.p. 80°–140°.

the corresponding dicyclohexylamine salt, m.p. 112°-114°.

EXAMPLE 64

Synthesis of 2-Acetylthiomethyl-5-(p-methoxybenzyloxycarbonyl)amino pentanoic acid N-hydroxysuccinimide ester To a solution of 3.7 g. of 2-acetylthiomethyl-5-(p-methoxybenzyloxycarbonyl)aminopentanoic acid and 1.21 g. of N-hydroxysuccinimide in 60 ml. of dichloromethane at 0°-5° is added 2.16 g. of N,N'-dicyclohexylcarbodiimide over twenty minutes with stirring. The resulting mixture is stirred overnight at 0°-5°. The precipitated dicyclohexylurea is filtered off, the filtrate concentrated in vacuo and the residue taken up in ethyl acetate and washed through a silica gel column to give 4.6 g. of 2-acetylthiomethyl-5-(p-methoxybenzyloxycarbonyl)amino pentanoic acid N-hydroxysuccinimide ester as an oil, which crystallises on trituration with ether. Recrystallization from ethyl acetate-hexane affords the analytical sample, m.p. 85°-87°.

EXAMPLE 65

Synthesis of N-[(2-Acetylthiomethyl-5-(p-methoxybenzyloxycarbonylamino)pentanoyl)]-L-proline tert-butyl ester By substituting 2-acetylthiomethyl-5-(p-methoxybenzyloxycarbonylamino)pentanoic acid for the N,S-diacetyl-D,L-cysteine in the procedure of Example 53, N-[2-acetylthiomethyl-5-(p-methoxybenzyloxycarbonylamino)pentanoyl]-L-proline tert-butyl ester is obtained.

EXAMPLE 66

Synthesis of N-(2-Acetylthiomethyl-5-aminopentanoyl)-L-proline, trifluoroacetate salt N-[2-Acetylthiomethyl-5-(p-methoxybenzyloxycarbonylamino)pentanoyl]-L-proline tert-butyl ester (2 g.) is dissolved in a mixture of trifluoroacetic acid (15 ml.) and anisole (6 ml.). The solution is stored at room temperature for one hour, the solvents are removed in vacuo and the residue is precipitated from ethyl acetate-ether to yield N-(2-acetylthiomethyl-5-aminopentanoyl)-L-proline, trifluoroacetate.

EXAMPLE 67

Synthesis of N-(5-Amino-2-mercaptomethylpentanoyl)-L-proline

N-(2-Acetylthiomethyl-5-aminopentanoyl)-L-proline trifluoroacetate (1 g.) is dissolved in a mixture of water (12 ml.) and concentrated ammonia (12 ml.) under a blanket of argon. The solution is stored twenty minutes at room temperature concentrated to 5 ml. and applied to a column of Dowex 50 ion exchange resin in the hydrogen cycle. The column is washed with water and N-(5-amino-2-mercaptomethylpentanoyl)-L-proline is eluted with a buffer of pyridine-acetic acid at pH 6.5.

EXAMPLE 68

By substituting the appropriate starting materials into Examples 53–67 and substantially following the procedures of Examples 53–67, the mercapto compounds, HS—Z (IV), defined in Table 8 are obtained.

TABLE 8

| | $R_4$ | $R_7$ | $R_8$ | $R_9$ | methylene bridge $R_8$-$R_9$ | $R_{23}$ | m | p |
|---|---|---|---|---|---|---|---|---|
| (1) | H | H | H | $CH_3$ | — | H | 1 | 0 |
| (2) | $CH_3$ | H | H | H | — | H | 1 | 0 |
| (3) | H | —CHO | $CH_3$ | $CH_2OH$ | — | $CH_3$ | 1 | 0 |
| (4) | $C_3H_7$ | H | H | —$CH_2CH_2CO_2H$ | — | H | 0 | 1 |
| (5) | H | $CH_3C(O)$— | — | — | $(CH_2)_3$ | H | 0 | 1 |
| (6) | H | H | H | (indol-3-yl)$CH_2$— | — | $C_2H_5$ | 0 | 1 |
| (7) | H | —C(=NH)—$NH_2$ | — | — | $(CH_2)_4$ | H | 1 | 1 |
| (8) | $C_2H_5$ | $C_2H_5C(O)$— | — | — | $(CH_2)_3$, 3-OH | $C_4H_9$ | 1 | 1 |
| (9) | H | H | H | —$(CH_2)_4NH_2$ | — | H | 1 | 1 |
| (10) | H | H | — | — | $(CH_2)_4$, 5-OH | H | 0 | 2 |
| (11) | H | $C_3H_7C(O)$— | $C_2H_5$ | (imidazol-4-yl)$CH_2$— | — | H | 0 | 2 |
| (12) | $CH_3$ | H | H | —$CH(CH_3)_2$ | — | H | 0 | 2 |
| (13) | $C_6H_5CH_2$ | H | H | —$CH_2CH(CH_3)_2$ | — | H | 1 | 2 |

TABLE 8-continued

| | R4 | R7 | R8 | R9 | methylene bridge R8-R9 | R23 | m | p |
|---|---|---|---|---|---|---|---|---|
| (14) | H | CH₃C(=O)— | — | — | (CH$_2$)$_3$, 4-F | CH$_3$ | 1 | 2 |
| (15) | H | H | H | —CH$_2$CH$_2$SCH$_3$ | — | H | 0 | 3 |
| (16) | CH$_3$ | —C(=NH)—NH$_2$ | CH$_3$ | HO—C$_6$H$_4$—CH$_2$— | — | H | 0 | 3 |
| (17) | H | H | H | C$_6$H$_5$CH$_2$ | — | H | 1 | 3 |
| (18) | H | C$_4$H$_9$C(=O)— | H | —CH$_2$SH | — | H | 1 | 3 |
| (19) | CH$_3$ | H | — | — | (CH$_2$)$_3$ | H | 0 | 4 |
| (20) | H | CH$_3$C(=O)— | H | —CH$_2$C(=O)—NH$_2$ | — | CH$_3$ | 0 | 4 |
| (21) | H | H | H | —CH$_2$(CH$_2$)$_2$NHC(=NH)NH$_2$ | — | H | 1 | 4 |
| (22) | H | HC(=O)— | —CH$_2$OH | CH$_3$ | — | H | 1 | 4 |

Examples 69–78 describe the synthesis of HS—Z where Z is defined by formula V. The procedures followed in these examples are described in U.S. Pat. No. 4,116,962.

EXAMPLE 69

Synthesis of 2-(Acetylthiomethyl)-3-(acetylthio)propanoic acid

A solution of 3.36 g. (40 mmoles) of thiolacetic acid in 40 ml. of N potassium hydroxide is added dropwise to a solution of 2-bromomethyl-3-bromopropanoic acid in 1.0N potassium hydroxide (20 ml). The mixture is stirred at room temperature overnight, acidified with concentrated hydrochloric acid and extracted with ethyl acetate. The organic layer is dried and concentrated in vacuo. The residue is converted into a dicyclohexylammonium salt (m.p. 116°–118°) and the salt converted back into the free acid, 2-(acetylthiomethyl)-3-(acetylthio)propanoic acid, by distribution between ethyl acetate and 10% potassium bisulfate.

EXAMPLE 70

Synthesis of N-[(2-Acetylthiomethyl)-3-(acetylthio)propanoyl]-L-proline

To a solution of L-proline (1.44 g.) and sodium carbonate (2.7 g.) in water (25 ml.) in an ice bath, 2-(acetylthiomethyl)-3-(acetylthio)propanoic acid chloride (3.9 g.-prepared from 2-(acetylthiomethyl)-3-(acetylthio)-propanoic acid and thionyl chloride) is added and the mixture is vigorously stirred at room temperature for two hours. After extraction with ethyl acetate, the aqueous layer is acidified and extracted with ethyl acetate. The organic layer is dried and concentrated to dryness. The residue is chromatographed on a column of silica gel with a mixture of benzene-acetic acid (7:1). The fractions containing the desired material are pooled and concentrated to dryness to yield N-[(2-acetylthiomethyl)-3-(acetylthio)-propanoyl]-L-proline as an oil (1.3 g). R$_f$: 0.3 (silica gel:benzene-acetic acid, 75:25).

EXAMPLE 71

Synthesis of N-(2-Mercaptomethyl-3-mercaptopropanoyl)-L-proline

N-[(2-Acetylthiomethyl-3-(acetylthio)propanoyl]-L-proline (1.2 g.) is dissolved in a mixture of water (12 ml.) and concentrated ammonia (12 ml.) under an atmosphere of argon. After twenty minutes, the mixture is acidified with concentrated hydrochloric acid. The crystalline precipitate N-(2-mercaptomethyl-3-mercaptopropanoyl)-L-proline is filtered and dried, yield 0.63 g., m.p. 138°–140°.

EXAMPLE 72

Synthesis of 3-(Acetylthio)-2-(methylthiomethyl)propanoic acid

A mixture of 3-(methylthiomethyl)acrylic acid (5.5 g.) and thiolacetic acid (5 ml.) is heated in the steam bath until disappearance of vinyl proton absorption in the nmr. The mixture is concentrated to remove the excess thiolacetic acid to obtain 3-(acetylthio)-2-(methylthiomethyl)propanoic acid.

EXAMPLE 73

Synthesis of N-[3-(Acetylthio)-2-(methylthiomethyl)propanoyl]-L-proline

To a solution of L-proline (1.44 g.) and sodium carbonate (2.7 g.) in water (25 ml.) in an ice bath, 3-(acetylthio)-2-(methylthiomethyl)propanoic acid chloride (prepared from the acid of Example 72 with thionyl chloride (3.6 g.) is added, and the mixture is vigorously stirred at room temperature for two hours. After extraction with ethyl acetate, the aqueous layer is acidified and extracted with ethyl acetate. The organic layer is dried and concentrated to dryness in vacuo to give N-[3-(acetylthio)-2-(methylthiomethyl)propanoyl]-L-proline.

EXAMPLE 74

Synthesis of N-[3-Mercapto-2-(methylthiomethyl)propanoyl]-L-proline

N-[3-(acetylthio)-2-(methylthiomethyl)propanoyl]-L-proline (1.2 g.) is dissolved in a mixture of water (12 ml.) and concentrated ammonia (12 ml.) under a blanket of argon. After twenty minutes, the reaction mixture is acidified and extracted with ethyl acetate. The organic layer is dried and concentrated to dryness to yield N-[3-(mercapto-2-methylthiomethyl)propanoyl]-L-proline.

EXAMPLE 75

Synthesis of N-(2-Hydroxymethyl-3-mercaptopropanoyl)-L-proline

N-[2-acetoxymethyl-3-(acetylthio)propanoyl]-L-proline (1.5 g.) is dissolved in a mixture of water (12 ml.) and concentrated ammonia (12 mk.) under a blanket of argon. After one hour, the reaction mixture is concentrated to ca. dryness, diluted with water and the solution applied to a column of cation exchange resin (Dowex 50) in the hydrogen cycle. The water eluate is concentrated to small volume and freeze dried to yield N-(2-hydroxymethyl-3-mercaptopropanoyl)-L-proline.

EXAMPLE 76

Synthesis of N-[2-Benzoylthio-3-methoxybutanoyl]-L-proline

To a solution of L-proline (5.75 g.) in N sodium hydroxide (50 ml.) chilled in an ice bath, 2N sodium hydroxide (25 ml.) and 2-bromo-3-methoxybutyric acid chloride [obtained from 2-bromo-3-methoxybutyric acid [*J. Am. Chem. Soc.*, 71, 1096, (1949)] and thionyl chloride] (10.7 g.) are added, with vigorous stirring. After three hours, thiobenzoic acid (7.5 g.) and potassium carbonate (4.8 g.) are added and the mixture is stirred at room temperature overnight. The reaction mixture is acidified and extracted with ethyl acetate. The organic layer is concentrated to dryness and the residue is chromatographed on a column of silica gel with benzene-acetic acid to yield N-[2-benzoylthio-3-methoxybutanoyl]-L-proline.

EXAMPLE 77

Synthesis of N-[2-Mercapto-3-methoxybutanoyl]-L-proline

By substituting N-[2-benzoylthio-3-methoxybutanoyl]L-proline for the N-[3-acetylthio-2-(methylthiomethyl)propanoyl]-L-proline in the procedure of Example 74, N-[2-mercapto-3-methoxybutanoyl]-L-proline is obtained.

EXAMPLE 78

By substituting the appropriate starting materials into Examples 69–77 and substantially following the procedures of Examples 69–77, the mercapto compounds, HS—Z (V), defined in Table 9 are obtained.

TABLE 9

| | X | $R_{10}$ | $R_{11}$ | $R_8$ | $R_9$ | methylene bridge $R_8$—$R_9$ | $R_{23}$ | m | p |
|---|---|---|---|---|---|---|---|---|---|
| (1) | S | — | $C_2H_5$ | H | H | — | H | 0 | 0 |
| (2) | O | — | H | — | — | $(CH_2)_3$ | $CH_3$ | 0 | 0 |
| (3) | S | — | HC(=O)— | H | —$CH_2CO_2H$ | — | H | 1 | 0 |
| (4) | O | — | H | — | — | $(CH_2)_3$, 3-Cl | H | 1 | 0 |
| (5) | S | $C_2H_5$ | H | $CH_3$ | —CH(OH)CH$_3$ | — | H | 0 | 1 |
| (6) | S | H | $CH_3$ | H | 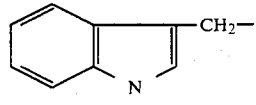 | — | H | 1 | 1 |
| (7) | O | H, $CH_3$ | $C_4H_9$ | — | — | $(CH_2)_4$ | $C_2H_5$ | 0 | 2 |
| (8) | S | H | $CH_3C(=O)$— | H | —$CH_2SH$ | — | H | 0 | 2 |
| (9) | S | H | H | $CH_2OH$ | $(CH_2)_4NH_2$ | — | H | 1 | 2 |
| (10) | O | $CH_3$, H | $C_3H_7$ | — | — | $(CH_2)_3$, 3-OH | $C_4H_9$ | 1 | 2 |
| (11) | S | H | $C_2H_5C(=O)$— | H | 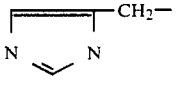 | — | H | 0 | 3 |
| (12) | S | H, H, $C_3H_7$ | H | H | —CH(CH$_3$)$_2$ | — | H | 0 | 3 |
| (13) | S | H | $C_3H_7C(=O)$— | — | — | $(CH_2)_4$, 5.OH | H | 1 | 3 |
| (14) | O | H | H | H | $CH_3SCH_2$ | — | $CH_3$ | 1 | 3 |
| (15) | O | H | $CH_3$ | $C_3H_7$ | —$CH_2CH_2SCH_3$ | — | H | 0 | 4 |

TABLE 9-continued

| | X | $R_{10}$ | $R_{11}$ | $R_8$ | $R_9$ | methylene bridge $R_8$—$R_9$ | $R_{23}$ | m | p |
|---|---|---|---|---|---|---|---|---|---|
| (16) | O | H | H | — | — | $(CH_3)_2$ | H | 0 | 4 |
| (17) | O | H | H | H | —CH(CH$_3$)(C$_2$H$_5$) | — | H | 1 | 4 |
| (18) | S | H | $\underset{CH_3C—}{\overset{O}{\underset{\|}{\|}}}$ | H | CH$_3$ | — | H | 1 | 4 |

Examples 79–86 describe the synthesis of HS—Z where Z is defined by formula VI. The procedures followed in these examples are described in U.S. Pat. No. 4,091,024.

EXAMPLE 79

Synthesis of 3-acetylthio-2-methoxycarbonylmethyl propanoic acid

A mixture of thiolacetic acid (12.5 g.) and 3-methoxycarbonyl-2-methylenepropanoic acid (17.1 g.) are heated on a steam bath for two hours. The reaction is concentrated in vacuo and the residue is dissolved in ethyl acetate (125 ml.) and dicyclohexylamine (35 ml.) is added. The crystals are filtered, dried and recrystallized from ethyl acetate to yield 37.8 g., m.p. 120°–121°. This dicyclohexylammonium salt of 3-acetylthio-2-methoxycarbonylmethylpropanoic acid is converted to the free acid by distribution between a system of ethyl acetate and 10% aqueous potassium bisulfate.

EXAMPLE 80

Synthesis of N-[3-(acetylthio)-2-(methoxycarbonylmethyl)-propanoyl]-L-proline t-butyl ester To a solution of L-proline t-butyl ester (1.71 g.) and 3-hydroxybenzotriazole (1.35 g.) in dichloromethane (15 ml.) dicyclohexylcarbodiimide (2.06 g.) and the product from Example 79 (2.2 g.) are added. After 18 hours stirring at room temperature, the precipitate formed is filtered off, the filtrate is washed neutral, dried and concentrated to dryness to yield 3.7 g. of the named product R$_f$: 0.8 (silica gel-ethyl acetate).

EXAMPLE 81

Synthesis of N-[3-(acetylthio)-2-(methoxycarbonylmethyl)-propanoyl]-L-proline 2.9 g. of the product from Example 80 is dissolved in a mixture of trifluoroacetic acid (17.5 ml.) and anisole (8.4 ml.). After one hour storage at room temperature, the excess trifluoroacetic acid is removed in vacuo and the residue is precipitated twice from ether-hexane to yield 2.1 g. of the named product. R$_f$: 0.4 (silica gel-benzene:acetic acid, 75.25).

EXAMPLE 82

Synthesis of N-[3-Mercapto-2-(methoxycarbonylmethyl)-propanoyl]-L-proline 2.1 g. of the product from Example 81 is dissolved in a mixture of water (35 ml.) and concentrated ammonia (35 ml.) under a blanket of argon. After 20 minutes, the solution is chilled in an ice bath, made acidic with concentrated hydrochloric acid, saturated with sodium chloride and extracted with ethyl acetate. The organic layer is dried and concentrated to dryness in vacuo to yield 1.1 g. of the named product that is purified by chromatography on silica gel (benzene:acetic acid 75:25) R$_f$: 0.35 (silica gel-benzene:acetic acid, 75:25).

EXAMPLE 83

Synthesis of N-[2-Carboxymethyl-3-mercaptopropanoyl]-L-proline

To a solution of the product from Example 81 (3.0 g.) in methanol (60 ml.), 1N sodium hydroxide (60 ml.) is added. After 4 hours, the solution is applied to a column of Dowex 50 ion exchange resin in the hydrogen cycle, and the desired material is eluted with water to yield 2.3 g. of the named product R$_f$: 0.2 (silica gel-benzene:acetic acid, 75:25).

EXAMPLE 84

Synthesis of N-[2-carbamoylmethyl-3-mercaptopropanoyl]-L-proline 2.1 g. of the product from Example 81 is dissolved in a mixture of water (40 ml.) and concentrated ammonia (40 ml.). After one hour the reaction mixture is concentrated to ⅓ volume, and applied to a column of Dowex 50 resin in the hydrogen cycle. The product is eluted with water. The aqueous is extracted with ethyl acetate and then concentrated to dryness to yield 1.4 g. of the named product R$_f$: 0.50 (silica gel-Chloroform:methanol:acetic acid:water).

EXAMPLE 85

Synthesis of N-[2-([N-butylcarbomoyl]methyl)-3-mercaptopropanoly]-L-proline

By substituting 3-(acetylthio)-2-[(N-butylcarbomoyl)methyl]propanoic acid for the 3-(acetylthio)-2-(methoxycabonylmethyl)propanoic acid in Example 80 and substantially following the procedures of Examples 80–82, the named product is obtained.

EXAMPLE 86

By substituting the appropriate starting materials into Examples 79–85 and substantially following the procedures of Examples 79–85, the mercapto compounds, HS—Z (VI), defined in Table 10 are obtained.

TABLE 10

| | $R_{12}$ | $R_8$ | $R_9$ | methylene bridge $R_8$—$R_9$ | $R_{23}$ | m | p |
|---|---|---|---|---|---|---|---|
| (1) | CN | H | CH$_3$ | — | H | 0 | 0 |
| (2) | CO$_2$H | H | H | — | H | 0 | 0 |

TABLE 10-continued

| | $R_{12}$ | $R_8$ | $R_9$ | methylene bridge $R_8$—$R_9$ | $R_{23}$ | m | p |
|---|---|---|---|---|---|---|---|
| (3) | $-\overset{\overset{O}{\|}}{C}-NHC_3H_7$ | $C_2H_5$ | $-CH(CH_3)_2$ | — | $CH_3$ | 1 | 0 |
| (4) | $-\overset{\overset{O}{\|}}{C}-OC_2H_5$ | — | — | $(CH_2)_4$ | H | 1 | 0 |
| (5) | $-\overset{\overset{O}{\|}}{C}-NH_2$ | H | $-CH_2OH$ | — | H | 0 | 1 |
| (6) | $CO_2H$ | H | $(CH_2)_4NH_2$ | — | H | 0 | 1 |
| (7) | $-\overset{\overset{O}{\|}}{C}-OC_5H_{11}$ | — | — | $(CH_2)_3$, 3-OH | H | 0 | 2 |
| (8) | $-\overset{\overset{O}{\|}}{C}-NHCH_3$ | H | indolyl-CH$_2$ | — | H | 0 | 2 |
| (9) | $-\overset{\overset{O}{\|}}{C}-NH_2$ | $C_3H_7$ | $-CH_2-SH$ | — | H | 1 | 2 |
| (10) | CN | H | $-CH_2\overset{\overset{O}{\|}}{C}-NH_2$ | — | $C_2H_5$ | 1 | 2 |
| (11) | $CO_2H$ | — | — | $(CH_2)_4$, 4-OH | H | 0 | 3 |
| (12) | $-\overset{\overset{O}{\|}}{C}-NH$ | H | $-CH_2CO_2H$ | — | H | 0 | 3 |
| (13) | CN | H | $-(CH_2)_3NH\overset{\overset{NH}{\|}}{C}NH_2$ | — | H | 1 | 3 |
| (14) | $-\overset{\overset{O}{\|}}{C}-OCH_3$ | H | imidazolyl-CH$_2$ | — | H | 0 | 4 |
| (15) | $-\overset{\overset{O}{\|}}{C}-NHC_2H_5$ | $CH_3$ | $C_6H_5CH_2-$ | — | H | 1 | 4 |

The following examples describe the synthesis of R—A—S—Z.

EXAMPLE 87

Synthesis of $N^\alpha$-[3-($N^\alpha$-benzoyl-5-methyl-tryptophyl)thioacetyl]-L-proline A solution of 10 mmoles of $N^\alpha$-benzoyl-5-methyl-tryptophan in redistilled dimethylformamide (DMF) is cooled in an ice-dry ice-acetone bath at $-20°$ C. To this solution is added a cold solution of 10 mmoles of 1,1'-carbonyldiimidazole in DMF. The solution is stirred at $-10°$ C. for two hours and then added to a cold solution of 10 mmoles of N-(2-mercaptoacetyl)-L-proline (from Example 17) in DMF which is neutralized with N-ethyl morpholine. The reaction mixture is stirred at $-10°$ C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO$_4$. The product is purified by liquid chromatography on Sephadex LH-20 using a 1.2 cm by 95 cm column and eluted with isopropanol. The peak fractions are pooled and the solvent removed under reduced pressure yielding the named product, as a foam-like material.

EXAMPLE 88

Synthesis of $N^\alpha$-([2-($N^\alpha$-benzoyl-phenylglycyl)thioethyl]sulfonyl)-L-proline A solution of 5 mmoles of $N^\alpha$-benzoyl-phenylglycine in redistilled dimethylformamide (DMF) is cooled in an ice-dry ice-acetone bath at $-20°$ C. To this solution is added a cold solution of 5 mmoles of 1,1'-carbonyldiimidazole in DMF. The solution is stirred at $-10°$ C. for two hours and then mixed with a cold solution of 5 mmoles of N-[(2-mercaptoethyl)sulfonyl]-L-proline (from Example 28) in DMF which is neutralized with N-ethyl morpholine. The reaction mixture is stirred at $-10°$ C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO$_4$. The product is purified by liquid chromatography on Sephadex LH-20 using a 1.2 cm by 95 cm column and eluted with THF:isopropanol, 3:7 (parts by volume). The peak fractions are pooled and the solvent removed under reduced pressure yielding the named product.

EXAMPLE 89

Synthesis of
N$^\alpha$-[3-(N$^\alpha$-tert-butyloxycarbonyl-4-nitrophenylalanyl-thio)-2-trifluoromethylpropanoyl]-L-proline A solution of 15 mmoles of N$^\alpha$-tert-butyloxycarbonyl-4-nitrophenylalanine (N$^\alpha$-Boc-4-nitro-phenylalanine in redistilled dimethylformamide (DMF) is cooled in an ice-dry ice-acetone bath at −20° C. To this solution is added a cold solution of 15 mmoles of 1,1′-carbonyldiimidazole in DMF. The solution is stirred at −10° C. for two hours and then mixed with a cold solution of 15 mmoles of N-(3-mercapto-2-trifluoromethyl)propanoyl-L-proline (from Example 33) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO$_4$. The product is purified by liquid chromatography on Sephadex G-10 using a 1.2 cm by 95 cm column and eluted with THF:isopropanol, 3:7 (parts by volume). The peak fractions are pooled and the solvent removed under reduced pressure yielding the named product.

EXAMPLE 90

Synthesis of
N$^\alpha$-(3-[4-nitro-phenylalanyl]thio-2-trifluoromethyl-propanoyl)-L-proline The product from Example 89 is deprotected by stirring a mixture of 30 mg of the product, 50 ul of anisole and 200 ul of anhydrous trifluoroacetic acid (TFA) at room temperature for one hour. Anisole and TFA are removed under reduced pressure at 35° C. and the residue is triturated with anhydrous ether. The residue is purified by liquid chromatography on Sephadex G-10 using a 1.2 cm by 95 cm column and eluted with 5% acetic acid. The peak fractions are pooled and freeze-dried yielding the named compound.

EXAMPLE 91

Synthesis of
N$^\alpha$-([3-(N$^\alpha$-acetyl-3-chloro-tyrosylthio)-1-oxopropyl-]amino)-L-proline A solution of 20 mmoles of N$^\alpha$-acetyl-3-chloro-tyrosine in redistilled dimethylformamide (DMF) is cooled in an ice-dry ice-acetone bath at −20° C. To this solution is added a cold solution of 20 mmoles of 1,1′-carbonyldiimidazole in DMF. The solution is stirred at −10° C. for two hours and then is added to a cold solution of 20 mmoles of N-[(3-mercapto-1-oxopropyl-)amino]-L-proline (from Example 39) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCL and then three times with saturated NaCl solution. The organic solvent is removed with a rotary evaporator after drying over anhydrous MgSO$_4$. The product is purified by Sephadex LH-20 column chromatography using a 1.2 cm by 95 cm column and eluted with isopropanol. The peak fractions are pooled and the solvent is removed under reduced pressure yielding the named product.

EXAMPLE 92

Synthesis of N$^\alpha$-[3-(N$^\alpha$-cyclopentanecarbonyl-O-benzyltyrosylthio)-2-ethylpropanoyl]-L-3,4-dehydroproline A solution of 5 mmoles of N$^\alpha$-cyclopentanecarbonyl-O-benzyl tyrosine in redistilled dimethylformamide (DMF) is cooled in an ice-dry ice-acetone bath at −20° C. To this solution is added a cold solution of 5 mmoles of 1,1′-carbonyldiimidazole in DMF. The solution is stirred at −10° C. for two hours and then mixed with a cold solution of 5 mmoles of N-(2-ethyl-3-mercapto-propanoyl)-L-3,4-dehydroproline (from Example 42) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled and washed with 0.1N HCl and then three times with saturated NaCl solution. The solvent is removed with a rotary evaporator after drying over anhydrous MgSO$_4$. The product is purified by LH-20 column chromatography using a 1.2 cm by 95 cm column and eluted with isopropanol. The peak fractions are pooled and the solvent is removed under reduced pressure yielding the named product.

EXAMPLE 93

Synthesis of
([3-(N$^\alpha$-cyclopentanecarbonyl-N$^\epsilon$-tert-butyloxycarbonyl-L-lysyl-$\beta$-2-thienyl-alanyl)thiopropanoyl]amino)-2-methylpropanoic acid A solution of 10 mmoles of N$^\alpha$-cyclopentanecarbonyl-N$^\epsilon$-tert-butyloxycarbonyl-L-lysyl-$\beta$-2-thienyl-alanine in redistilled dimethylformamide (DMF) is cooled in an ice-dry ice-acetone bath at −20° C. To this solution is added a cold solution of 10 mmoles of 1,1′-carbonyldiimidazole in DMF. The solution is stirred at −10° C. for two hours and then mixed with a cold solution of 10 mmoles of 2-[(3-mercaptopropanoyl-)amino]-2-methylpropanoic acid (from Example 46) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice water bath and washed with 1N citric acid and then three times with saturated NaCl solution. The solvent is removed with a rotary evaporator after drying over anhydrous MgSO$_4$. The product is purified by LH-20 column chromatography using a 1.2 cm by 95 cm column and eluted with THF:isopropanol, 3:7 (parts by volume). The peak fractions are pooled and the solvent is removed under reduced pressure yielding the named product.

EXAMPLE 94

Synthesis of ([3-(N$^\alpha$-cyclopentanecarbonyl-L-lysylthiopropanoyl]amino)-2-methylpropanoic acid The N$^\epsilon$-Boc group is removed from the lysine by stirring a mixture of 30 mg of the product from Example 93 with 50 ul anisole and 200 ul of anhydrous trifluoroacetic acid (TFA) at room temperature for one hour. Anisole and TFA are removed under reduced pressure at 35° C. and the resude is triturated with anhydrous ether. The residue is purified by liquid chromatography on Sephadex G-10 using a 1.2 cm by 95 cm column and eluted with 5% acetic acid. The peak fractions are pooled and freeze-dried yielding the named product.

EXAMPLE 95

Preparation of N$^\alpha$-[3-(Pyro-L-glutamyl-3,5-dibromo-tyrosy)]-thiopropanoyl-L-alanine A solution of 5 mmoles of 1,1'-carbonyldiimidazole in DMF is added to a solution of 5 mmoles of pyro-L-glutamyl-3,5-dibromo-tyrosine in DMF at −15° C. The reaction mixture is stirred at −10° C. for 1 hour, and then a mixture of 5 mmoles of N-(3-mercaptopropanoyl)-L-alanine (from Example 50), neutralized with N-ethyl morpholine in DMF, is added. The reaction mixture is stirred at −10° C. for an additional hour and then is slowly warmed to room temperature. DMF is removed under reduced pressure with a rotary evaporator at 40° C. and then ethyl acetate:1N citric acid (7:2) are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2 cm×99 cm) partition column chromatography with n-butanol:acetic acid:H$_2$O (4:1:5 by volume) yielding the named product.

EXAMPLE 96

Preparation of N$^\alpha$-([2-(L-lysyl-6-fluoro-tryptophyl)thiomethyl]-5-aminopentanoyl)-L-proline A solution of 15 mmoles of 1,1'-carbonyldiimidazole in DMF is added to a solution of 15 mmoles of bis-Boc-L-lysyl-6-fluoro-tryptophyl in DMF at −15° C. The reaction mixture is stirred at −10° C. for 1 hour, and then a mixture of 15 mmoles of N-(5-N-Boc-amino-2-mercaptomethylpentanoyl)-L-proline (from Example 67), neutralized with N-ethyl morpholine in DMF, is added. The reaction mixture is stirred at −10° C. for an additional hour and then is slowly warmed to room temperature. DMF is removed under reduced pressure with a rotary evaporator at 40° C. and then ethyl acetate:1N citric acid (7:2) are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2×99 cm) partition column chromatography with n-butanol:acetic acid:H$_2$O (4:1:5 by volume). The Boc protecting groups are removed by treatment with trifluoroacetic acid in anisole as substantially described in Example 90 to yield the named product.

EXAMPLE 97

Preparation of N$^\alpha$-[(3-(L-arginyl-5-methoxy-tryptophyl]thio)-2-(methyl-thiomethyl)propanoyl]-L-proline A solution on 10 mmoles of 1,1'-carbonyldiimidazole in DMF is added to a solution of 10 mmoles of tri-Adoc-L-arginyl-5-methoxy-tryptophan in 0.5 ml DMF at −15° C. The reaction mixture is stirred at −10° C. for 1 hour, and then a mixture of 10 mmoles of N-[3-mercapto-2-(methylthiomethylpropanoyl]-L-proline (from Example 74), neutralized with N-ethyl morpholine in DMF, is added. The reaction mixture is stirred at −10° C. for an additional hour and then is slowly warmed to room temperature. DMF is removed under reduced pressure with a rotary evaporator at 40° C. and then 7 ml ethyl acetate and 2 ml 1N citric acid are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2 cm×99 cm) partition column chromatography with n-butanol:acetic acid:-H$_2$O (4:1:5 by volume). The tri-Adoc protecting group is removed by treatment with trifluoroacetic acid in anisole as substantially described in Example 90 to yield the named product.

EXAMPLE 98

Synthesis of N$^\alpha$-[(3-[N$^\alpha$-pyro-L-glutamyl-L-lysyl-3,5-dibromo-tyrosyl]-thio)-2-(methoxycarbonylmethyl)propanoyl]-L-proline A solution of 5 mmoles of N$^\alpha$-pyro-L-glutamyl-N$^\epsilon$-tert-butyloxycarbonyl-L-lysyl-3,5-dibromo-tyrosine in redistilled dimethylformamide (DMF) is cooled in an ice-dry ice-acetone bath at −20° C. To this solution is added a cold solution of 5 mmoles of 1,1'-carbonyldiimidazole in DMF. The solution is stirred at −10° C. for two hours and then mixed with a cold solution of 5 mmoles of N-[3-mercapto-2-(methoxycarbonylmethyl)propanoyl]-L-proline (from Example 82) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice water bath and washed with 1N citric acid and then three times with saturated NaCl solution. The solvent is removed with a rotary evaporator after drying over anhydrous MgSO$_4$. The product is purified by LH-20 column chromatography using a 1.2 cm by 95 cm column and eluted with THF:isopropanol, 3:7 (parts by volume). The peak fractions are pooled and the solvent is removed under reduced pressure yielding the product N$^\alpha$[(3-[N$^\alpha$-pyro-L-glutamyl-N$^\epsilon$-tert-butyloxycarbonyl-L-lysylphenylalanyl]-thio-2-(methoxycarbonylmethyl)propanoyl]-L-proline. The tert-butyloxycarbonyl protecting group is removed as described in Examples 94 to yield the named product.

EXAMPLE 99

By substituting the appropriate starting materials from Examples 1–86 using appropriate blocking groups where necessary into Examples 87–98 and substantially following the procedures of Examples 87–98, the following thioester compounds, R—A—S—Z, as defined in the following table are obtained.

TABLE 11

| R | A | Z |
|---|---|---|
| t-butyloxycarbonyl | 3-hydroxy-tyrosine | Ex. 19 |
| L-lysyl | β-benzyl aspartic acid | Ex. 26 (6) |
| formyl | α-methyl phenylalanine | Ex. 26 (14) |
| butanoyl | thyronine | Ex. 26 (23) |
| H | 1-methyl-tryptophan | Ex. 29 (3) |
| benzoyl | 3-fluoro-tyrosine | Ex. 29 (10) |
| pyro-L-glutamyl | phenylglycine | Ex. 34 |
| cyclopentane carbonyl-L-lysyl | S—benzylecysteine | Ex. 35 (1) |
| phenylpropanoyl | γ-benzyl glutamate | Ex. 35 (12) |
| L-arginyl | 4-amino-phenylalanine | Ex. 40 (5) |
| H | α-methyl tryptophan | Ex. 40 (11) |
| formyl | β-phenyl serine | Ex. 40 (15) |
| cyclotentanecarbonyl | O—benzyl tyrosine | Ex. 44 (1) |
| benzoyl | 3-nitro-tyrosine | Ex. 44 (5) |
| t-butyloxcarbonyl | 5-fluoro-tyrptophan | Ex. 44 (11) |
| pyro-L-glutamyl-L-tysyl | 3,5-dichloro-tyrosine | Ex. 47 |
| H | O—benzyl threonine | Ex. 48 (6) |
| benzoyl | 4-methoxy-phenylalanine | Ex. 52 (3) |
| L-lysyl | α-methyl histidine | Ex. 52 (10) |
| acetyl | 3-chloro-5-bromo-tyrosine | Ex. 52 (16) |
| cyclopentanecarbonyl | 4-iodo-phenylalanine | Ex. 67 |
| L-lysyl | 3-methoxy-tyrosine | Ex. 68 (4) |
| benzoyl | α-methyl tyrosine | Ex. 68 (11) |
| propanoyl | O—benzyl serine | Ex. 68 (16) |
| cyclopentanecarbonyl-L-lysyl | 4-nitro-phenylalanine | Ex. 73 |
| H | β-2-thienyl-serine | Ex. 78 (5) |
| benzoyl | 3-methoxy-tryptophan | Ex. 86 (6) |
| t-butyloxycarbonyl | β-2-thienyl-alanine | Ex. 86 (13) |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A new compound having the general formula R—A—S—Z wherein,

R is hydrogen, formyl, acetyl, propanoyl, butanoyl, phenylacetyl, phenylpropanoyl, benzoyl, cyclopentanecarbonyl, tert-butyloxycarbonyl, cyclopentanecarbonyl-L-lysyl, pyro-L-glutamyl-L-lysyl, L-arginyl, L-lysyl or pyro-L-glutamyl;

A is a divalent moiety derived from phenylglycine, β-benzyl aspartic acid, γ-benzyl glutamic acid, S-benzyl cysteine, O-benzyl aspartic acid, O-benzyl tyrosine, O-benzyl threonine, β-phenyl serine, thyronine, β-2-thienylserine, β-2-thienylalanine, α-methyl histidine, α-methyl tyrosine, α-methyl phenylalanine, α-methyl tryptophan, substituted tyrosine wherein the substituent is halo, nitro, methoxy or hydroxy, or substituted phenylaline wherein the substituent is selected from nitro, amino and methoxy or substituted tryptophan wherein the substituent is selected from methyl and methoxy, the α-amino group of which moiety is in amide linkage with R when R is acyl, and forms a primary amino group with R when R is H, and the carboxyl group of which moiety is in thioester linkage with S;

S is a sulfur atom joined in thioester linkage to A; and Z is selected from the following:

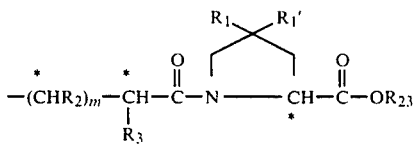

wherein,
(i) $R_1$ and $R_1'$ are each hydrogen or halogen, and $R_2$ and $R_3$ are each hydrogen, lower alkyl or trifluoromethyl provided that only one of $R_2$ and $R_3$ may be trifluoromethyl and further provided that at least one of $R_1$, $R_1'$, $R_2$ and $R_3$ must be halogen or trifluoromethyl
(ii) $R_{23}$ is hydrogen or lower alkyl and
(iii) m is 0 or 1;

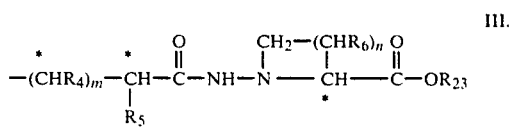

wherein
(i) $R_4$ and $R_5$ are each hydrogen, lower alkyl or phenyl-lower alkylene
(ii) N is 1, 2 or 3
(iii) $R_6$ is hydrogen or hydroxy or when n is 2, $R_6$ may also be halogen and
(iv) m and $R_{23}$ are as stated in II. above;

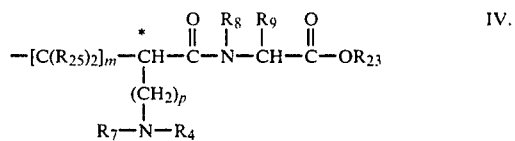

wherein
(i) $R_7$ is hydrogen, lower alkanoyl or amino (imino)-methyl;
(ii) p is 0 or an integer of from 1 to 4;
(iii) $R_{25}$ is hydrogen but when m is 1, p is 0, $R_4$ is hydrogen and $R_7$ is selected from hydrogen, lower alkyl and hydroxy lower alkylene; and $R_9$ is selected from hydrogen, lower alkyl, phenyl, phenyl-lower alkylene, hydroxy-lower alkylene, hydroxyphenyl-lower alkylene, mercapto-lower alkylene, lower alkyl-thio-lower alkylene, imidazolyl-lower alkylene, indolyl-lower alkylene, carbamoyl-lower alkylene and carboxy-lower alkylene, but $R_8$ and $R_9$ may together constitute a $(CH_2)_v$ bridge wherein v is 3 or 4, thus forming a 5 or 6-membered ring with the N and C to which $R_8$ and $R_9$ are respectively attached and in such instance when v is 3 one hydrogen of $(CH_2)_v$ may be replaced by OH or halogen and when v is 4, one such hydrogen may be replaced by OH;
(v) m and $R_{23}$ are each as defined in II. above; and
(vi) $R_4$ is as defined in III. above, provided further, however, that m and p may not both be 0;

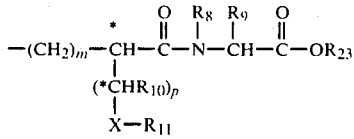

V.

wherein
(i) $R_{10}$ is hydrogen or lower alkyl;
(ii) $R_{11}$ is hydrogen, lower alkyl or lower alkanoyl
(iii) X is 0 or S;
(iv) m and $R_{23}$ are as stated in II. above, and
(v) $R_8$, $R_9$ and p are as stated in IV. above;

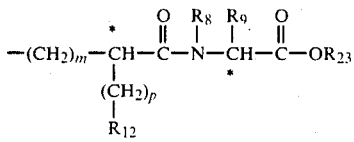

VI.

wherein
(i) $R_{12}$ is selected from carboxy, lower alkoxycarbonyl, carbamoyl, N-substituted carbamoyl and cyano;
(ii) m and $R_{23}$ are as stated in II. above; and
(iii) $R_8$, $R_9$ and p are as stated in IV. above.

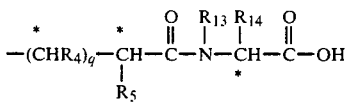

VII.

wherein
(i) $R_{13}$ is hydrogen, lower alkyl or phenyl-lower alkylene;
(ii) $R_{14}$ is selected from hydrogen, lower alkyl, phenyl-lower alkylene, hydroxy-lower alkylene, amino-lower alkylene, guanidino-lower alkylene, imidazolyl-lower alkylene, indolyl-lower alkylene, mercapto-lower alkylene, lower alkyl-thio-lower alkylene, carbamoyl-lower alkylene and carboxy-lower alkylene;
(iii) $R_4$ and $R_5$ are each as stated in III. above; and
(iv) q is 0, 1 or 2;

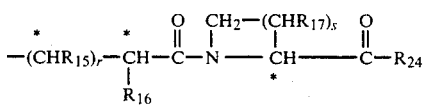

VIII.

wherein
(i) $R_{15}$ and $R_{16}$ are each hydrogen, lower alkyl, phenyl or phenyl-lower alkylene;
(ii) r is 0, 1 or 2;
(iii) s is 1, 2 or 3;
(iv) $R_{17}$ is hydrogen, hydroxy or lower alkyl and when s is 2, $R_{17}$ may also be halogen;
(v) $R_{24}$ is hydroxy, amino or lower alkoxy;

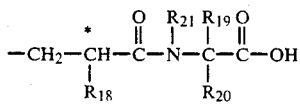

IX.

wherein
(i) $R_{18}$ is hydrogen or lower alkyl;
(ii) $R_{19}$ and $R_{20}$ are each lower alkyl and may together constitute a $(CH_2)_w$ bridge wherein w is 4, to form a ring of 5-carbons with the carbon to which they are each attached;
(iii) $R_{21}$ is hydrogen or lower alkyl and may constitute with $R_{19}$ a $(CH_2)_x$ bridge wherein x is 3, to form a five-membered ring with the N and C to which they are respectively attached;

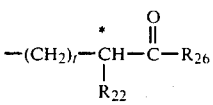

X.

wherein
(i) $R_{22}$ is hydrogen or lower alkyl;
(ii) t is 0 or 1; and
(iii) $R_{26}$ is selected from

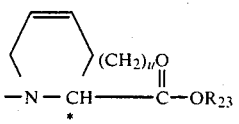

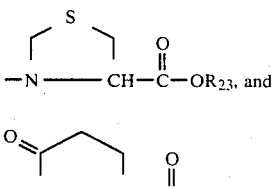, and

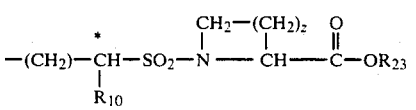

wherein u is 0 or 1 and $R_{23}$ is as defined for formula II., above;

$$-(CH_2)-\overset{*}{CH}-SO_2-N\underset{R_{10}}{\overset{CH_2-(CH_2)_z}{|}}CH-\overset{O}{\overset{\|}{C}}-OR_{23}$$

XI.

wherein
(i) z is 2 or 3;
(ii) $R_{10}$ is as stated in V. above; and
(iii) $R_{23}$ is as stated in II. above.

2. The compound of claim 1 wherein R is hydrogen, acetyl, benzoyl, cyclopentanecarbonyl, tert-butyloxycarbonyl, cyclopentanecarbonyl-L-lysyl or pyro-L-glutamyl.

3. The compound of claim 1 wherein Z is defined by formula II.

4. The compound of claim 1 wherein Z is defined by formula III.

5. The compound of claim 1 wherein Z is defined by formula IV.

6. The compound of claim 1 wherein Z is defined by formula V.

7. The compound of claim 1 wherein Z is defined by formula VI.

8. The compound of claim 1 wherein Z is defined by formula VII.

9. The compound of claim 1 wherein Z is defined by formula VIII.

10. The compound of claim 1 wherein Z is defined by formula IX.

11. The compound of claim 1 wherein Z is defined by formula X.

12. The compound of claim 1 wherein Z is defined by formula XI.

13. The compound of claim 4 wherein n is 2.

14. The compound of claim 5, 6 or 7 wherein $R_8$ and $R_9$ together form a —CH$_2$CH$_2$CH$_2$— bridge which completes a ring of 5 atoms with the nitrogen and carbon to which they are attached, one carbon optionally bearing a hydroxy group or a halogen group.

15. The compound of claim 9 wherein s is 2.

16. The compound of claim 10 wherein $R_{19}$ and $R_{21}$ together form a —CH$_2$CH$_2$CH$_2$— bridge which completes a ring of 5 atoms with the nitrogen and carbon to which they are attached.

17. The compound of claim 11 wherein $R_{26}$ is

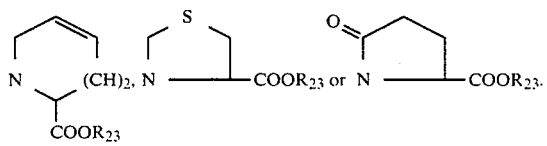

18. The compound of claim 12 wherein z is 2.

19. A method for inhibiting angiotensin converting enzyme in vivo which comprises administering to a mammal in need thereof a therapeutically effective dose of the compound of claim 1.

20. A method for inhibiting angiotensin converting enzyme in vivo which comprises administering to a mammal in need thereof a therapeutically effective dose of the compound of claim 2.

21. A method for inhibiting angiotensin converting enzyme in vivo which comprises administering to a mammal in need thereof a therapeutically effective dose of the compound of claim 3.

22. A method for inhibiting angiotensin converting enzyme in vivo which comprises administering to a mammal in need thereof a therapeutically effective dose of the compound of claim 4.

23. A method for inhibiting angiotensin converting enzyme in vivo which comprises administering to a mammal in need thereof a therapeutically effective dose of the compound of claim 5.

24. A method for inhibiting angiotensin converting enzyme in vivo which comprises administering to a mammal in need thereof a therapeutically effective dose of the compound of claim 6.

25. A method for inhibiting angiotensin converting enzyme in vivo which comprises administering to a mammal in need thereof a therapeutically effective dose of the compound of claim 7.

26. A method for inhibiting angiotensin converting enzyme in vivo which comprises administering to a mammal in need thereof a therapeutically effective dose of the compound of claim 8.

27. A method for inhibiting angiotensin converting enzyme in vivo which comprises administering to a mammal in need thereof a therapeutically effective dose of the compound of claim 9.

28. A method for inhibiting angiotensin converting enzyme in vivo which comprises administering to a mammal in need thereof a therapeutically effective dose of the compound of claim 10.

29. A method for inhibiting angiotensin converting enzyme in vivo which comprises administering to a mammal in need thereof a therapeutically effective dose of the compound of claim 11.

30. A method for inhibiting angiotensin converting enzyme in vivo which comprises administering to a mammal in need thereof a therapeutically effective dose of the compound of claim 12.

31. A method for inhibiting angiotensin converting enzyme in vivo which comprises administering to a mammal in need thereof a therapeutically effective dose of the compound of claim 13.

32. A method for inhibiting angiotensin converting enzyme in vivo which comprises administering to a mammal in need thereof a therapeutically effective dose of the compound of claim 14.

33. A method for inhibiting angiotensin converting enzyme in vivo which comprises administering to a mammal in need thereof a therapeutically effective dose of the compound of claim 15.

34. A method for inhibiting angiotensin converting enzyme in vivo which comprises administering to a mammal in need thereof a therapeutically effective dose of the compound of claim 16.

35. A method for inhibiting angiotensin converting enzyme in vivo which comprises administering to a mammal in need thereof a therapeutically effective dose of the compound of claim 17.

36. A method for inhibiting angiotensin converting enzyme in vivo which comprises administering to a mammal in need thereof a therapeutically effective dose of the compound of claim 18.

37. A method for reducing in vivo the blood pressure of a mammal in the hypertensive state which comprises administering a therapeutically effective dose of the compound of claim 1.

38. A method for reducing in vivo the blood pressure of a mammal in the hypertensive state which comprises administering a therapeutically effective dose of the compound of claim 2.

39. A method for reducing in vivo the blood pressure of a mammal in the hypertensive state which comprises administering a therapeutically effective dose of the compound of claim 3.

40. A method for reducing in vivo the blood pressure of a mammal in the hypertensive state which comprises administering a therapeutically effective dose of the compound of claim 4.

41. A method for reducing in vivo the blood pressure of a mammal in the hypertensive state which comprises administering a therapeutically effective dose of the compound of claim 5.

42. A method for reducing in vivo the blood pressure of a mammal in the hypertensive state which comprises administering a therapeutically effective dose of the compound of claim 6.

43. A method for reducing in vivo the blood pressure of a mammal in the hypertensive state which comprises administering a therapeutically effective dose of the compound of claim 7.

44. A method for reducing in vivo the blood pressure of a mammal in the hypertensive state which comprises administering a therapeutically effective dose of the compound of claim 8.

45. A method for reducing in vivo the blood pressure of a mammal in the hypertensive state which comprises administering a therapeutically effective dose of the compound of claim 9.

46. A method for reducing in vivo the blood pressure of a mammal in the hypertensive state which comprises administering a therapeutically effective dose of the compound of claim 10.

47. A method for reducing in vivo the blood pressure of a mammal in the hypertensive state which comprises administering a therapeutically effective dose of the compound of claim 11.

48. A method for reducing in vivo the blood pressure of a mammal in the hypertensive state which comprises administering a therapeutically effective dose of the compound of claim 12.

49. A method for reducing in vivo the blood pressure of a mammal in the hypertensive state which comprises administering a therapeutically effective dose of the compound of claim 13.

50. A method for reducing in vivo the blood pressure of a mammal in the hypertensive state which comprises administering a therapeutically effective dose of the compound of claim 14.

51. A method for reducing in vivo the blood pressure of a mammal in the hypertensive state which comprises administering a therapeutically effective dose of the compound of claim 15.

52. A method for reducing in vivo the blood pressure of a mammal in the hypertensive state which comprises administering a therapeutically effective dose of the compound of claim 16.

53. A method for reducing in vivo the blood pressure of a mammal in the hypertensive state which comprises administering a therapeutically effective dose of the compound of claim 17.

54. A method for reducing in vivo the blood pressure of a mammal in the hypertensive state which comprises administering a therapeutically effective dose of the compound of claim 18.

* * * * *

UNITED STATES PATENT AND TRADEMARK OFFICE
CERTIFICATE OF CORRECTION

PATENT NO. : 4,690,936
DATED : September 1, 1987
INVENTOR(S) : James W. Ryan and Alfred Chung It is certified that error appears in the above-identified patent and that said Letters Patent is hereby corrected as shown below:

Cover Page, Col 1, line 1 - insert of the following omitted

U.S. Patent Documents:

| U.S. Patent No. | Filing Date | Patentee |
|---|---|---|
| 3,865,934 | 4/1973 | Plotnikoff |
| 3,973,006 | 2/1975 | Ondetti |
| 3,976,770 | 2/1975 | Bumpus |
| 3,891,696 | 11/1973 | Bodor |
| 4,241,076 | 5/1979 | Ondetti et al. |
| 4,237,129 | 6/1979 | Ondetti et al. |
| 4,237,134 | 6/1979 | Ondetti et al. |
| 4,234,489 | 6/1979 | Ondetti et al. |
| 4,217,359 | 8/1979 | Krapcho |
| 4,216,209 | 3/1979 | Bellini et al. |
| 4,211,786 | 3/1979 | Rovnyak |

UNITED STATES PATENT AND TRADEMARK OFFICE
CERTIFICATE OF CORRECTION

PATENT NO. : 4,690,936
DATED : September 1, 1987
INVENTOR(S) : James W. Ryan and Alfred Chung It is certified that error appears in the above-identified patent and that said Letters Patent is hereby corrected as shown below:

| | | |
|---|---|---|
| 4,206,137 | 11/1978 | Condon et al. |
| 4,206,122 | 4/1978 | Natarajan |
| 4,206,121 | 12/1978 | Ondetti et al. |
| 4,199,512 | 9/1978 | Ondetti et al. |
| 4,198,517 | 12/1978 | Ondetti |
| 4,198,515 | 12/1978 | Ondetti |
| 4,198,509 | 10/1978 | Losee et al. |
| 4,192,878 | 5/1978 | Ondetti |
| 4,186,268 | 1/1979 | Petrillo |
| 4,179,434 | 6/1978 | Ondetti et al. |
| 4,177,277 | 9/1978 | Ondetti et al. |
| 4,173,704 | 5/1978 | Ondetti et al. |
| 4,112,119 | 3/1977 | Ondetti et al. |
| 4,127,729 | 2/1978 | Ondetti |
| 4,128,721 | 2/1978 | Ondetti |

UNITED STATES PATENT AND TRADEMARK OFFICE
CERTIFICATE OF CORRECTION

PATENT NO. : 4,690,936

DATED : September 1, 1987

INVENTOR(S) : James W. Ryan and Alfred Chung

It is certified that error appears in the above-identified patent and that said Letters Patent is hereby corrected as shown below:

| | | |
|---|---|---|
| 4,140,786 | 3/1978 | Ondetti et al. |
| 4,140,797 | 3/1978 | Ondetti et al. |
| 4,140,864 | 3/1978 | Ondetti et al. |
| 4,154,736 | 2/1978 | Ondetti et al. |
| 4,154,936 | 3/1978 | Ondetti et al. |
| 4,154,942 | 8/1978 | Ondetti et al. |
| 4,154,960 | 6/1978 | Ondetti et al. |
| 4,156,084 | 8/1978 | Ondetti et al. |
| 4,156,786 | 6/1978 | Ondetti et al. |
| 4,284,779 | 10/1977 | Ondetti et al. |
| 4,284,780 | 5/1978 | Ondetti et al. |
| 4,339,600 | 2/1978 | Ondetti et al. |
| 4,154,946 | 6/1978 | Ondetti et al. |
| 4,165,320 | 6/1978 | Ondetti et al. |
| 4,175,199 | 12/1978 | Ondetti et al. |

UNITED STATES PATENT AND TRADEMARK OFFICE
CERTIFICATE OF CORRECTION

PATENT NO. : 4,690,936

DATED : September 1, 1987

INVENTOR(S) : James W. Ryan and Alfred Chung

It is certified that error appears in the above-identified patent and that said Letters Patent is hereby corrected as shown below:

| | | |
|---|---|---|
| 4,176,291 | 12/1978 | Ondetti et al. |
| 4,192,945 | 3/1979 | Ondetti |
| 4,220,791 | 3/1979 | Rovnyak |
| 4,225,495 | 12/1978 | Ondetti |
| 4,235,885 | 6/1979 | Sundeen et al. |
| 4,261,895 | 10/1928 | Wiskett |
| 4,283,407 | 9/1978 | Malen et al. |
| 4,248,883 | 6/1979 | Sawayama et al. |
| 4,216,209 | 3/1979 | Bellini et al. |
| 4,179,568 | 7/1978 | Cohen et al. |
| 4,226,775 | 6/1979 | McEvoy et al. |
| 4,288,368 | 7/1979 | Haugwitz |
| 4,299,769 | 4/1980 | McEvoy |

UNITED STATES PATENT AND TRADEMARK OFFICE
CERTIFICATE OF CORRECTION

PATENT NO. : 4,690,936
DATED : September 1, 1987
INVENTOR(S) : James W. Ryan and Alfred Chung It is certified that error appears in the above-identified patent and that said Letters Patent is hereby corrected as shown below:

Cover Page - Col 1 - Insert the following omitted references:

Foreign Patent Documents:

| | | |
|---|---|---|
| 8000444 | 1/1980 | PCT |
| 2407204 | 10/1977 | FRANCE |
| 2018248 | 4/1979 | UK |
| 41632 | 4/1978 | JAPAN |
| 81116 | 7/1979 | JAPAN |
| 135093 | 10/1988 | JAPAN |

Cover page Col 2 - insert the following omitted

Other Publications:

Cronyn et al. J. Am. Chem. Soc., 74: 4726 (1952).
Lehninger A., Biochemistry , pp. 189-194 (1975).
Ryan, J.W. et al., Biochem J., 167:501 (1977).
Methoden der Organischem Chem (Houben-Weyl), vol. XV, Pt. 1, p. 376 et seq., (1974).

UNITED STATES PATENT AND TRADEMARK OFFICE
CERTIFICATE OF CORRECTION

PATENT NO. : 4,690,936
DATED : September 1, 1987
INVENTOR(S) : James W. Ryan and Alfred Chung It is certified that error appears in the above-identified patent and that said Letters Patent is hereby corrected as shown below:

Methoden der Organischem Chem (Houben-Weyl), vol, XV, Pt. II, p. 1 et seq., (1974).

Carter et al., J. Biol. Chem 138:627, (1941).

Engel et al., Proc. Soc. Exp. Biol. Med 143:483, (1973).

Jager et al., Chem. Ber. 103, 1727, (1970).

Klosterman et al., Biochem. 6, 170. (1967).

Lijinski et al., Tetrahedron 26, 5137 (1970).

Nagasawa et al., J. Med. Chem. 16, 583, (1973).

Mita et al., Chem. Pharm. Bull. 26, (4), 1333-1335, (1978).

Kripalani et al., Clin, Pharmacol. Ther. 27 (5), 636-641, (1980).

Pfister et al., J. Am. Chem. Soc. 71, 1096, (1949).

Merrifield, Avd Enzymol 32, 221, (1969).

Ricci et al., Anal Biochem. 79, 610, (1977).

Cushman, D.W. et al., Progr. Cardiovasc. Dis. 21, 176, (1978).

Oparil et al., Circ. Res 32, 415, (1973).

Oparil et al., Circ. Res 29, 682, (1971).

Dorer et al., Biochem. J. 141, 915, (1974)

UNITED STATES PATENT AND TRADEMARK OFFICE
CERTIFICATE OF CORRECTION

PATENT NO. : 4,690,936
DATED     : September 1, 1987
INVENTOR(S) : James W. Ryan and Alfred Chung It is certified that error appears in the above-identified patent and that said Letters Patent is hereby corrected as shown below:

Sharpless, S.K., "Hypnotics and Sedatives", The Pharmacological Basis of Therapeutics, The Macmillian Co., (1965), pp. 105-128.

Kripalani, K.J. et al., Abstracts, Joint Meeting of ASPET/SOT, Aug. 13-17, 1978.

Singhvi, S.M. et al., Abstracts, Joint Meeting of ASPET/SOT, Aug. 13-17, 1978.

Wong, K.K. and Dreyfuss, J., Abstracts, Joint Meeting of ASPECT/SOT, Aug. 13-17, 1978.

Buxton et al., J. Chem. Soc., p. 366 (1954)

Col 19, 9 delete "N-(3-methyl propanoyl)-L-proline" and insert -- N-(3-mercapto-2-methylpropanoyl)-L-Proline --.

Signed and Sealed this

Eighteenth Day of July, 1989

Attest:

DONALD J. QUIGG

Attesting Officer

Commissioner of Patents and Trademarks